US011291644B2

(12) United States Patent
Anthony et al.

(10) Patent No.: US 11,291,644 B2
(45) Date of Patent: Apr. 5, 2022

(54) PREVENTING PULMONARY RECURRENCE OF CANCER WITH LIPID-COMPLEXED CISPLATIN

(71) Applicants: Forrest H. Anthony, Villanova, PA (US); Matthew M. Parris, Plainsboro, NJ (US); Edwin J. Thomas, Moorestown, NJ (US); Guangtao Zhang, Princeton, NJ (US)

(72) Inventors: Forrest H. Anthony, Villanova, PA (US); Matthew M. Parris, Plainsboro, NJ (US); Edwin J. Thomas, Moorestown, NJ (US); Guangtao Zhang, Princeton, NJ (US)

(73) Assignee: ELEISON PHARMACEUTICALS, LLC, Princeton, NJ (US)

( * ) Notice: Subject to any disclaimer, the term of this patent is extended or adjusted under 35 U.S.C. 154(b) by 192 days.

(21) Appl. No.: 14/018,012

(22) Filed: Sep. 4, 2013

(65) Prior Publication Data
US 2014/0065205 A1  Mar. 6, 2014

Related U.S. Application Data

(60) Provisional application No. 61/743,398, filed on Sep. 4, 2012.

(51) Int. Cl.
A61K 31/282 (2006.01)
A61K 9/00 (2006.01)
A61K 33/243 (2019.01)

(52) U.S. Cl.
CPC .......... A61K 31/282 (2013.01); A61K 9/0078 (2013.01); A61K 33/243 (2019.01)

(58) Field of Classification Search
CPC .. A61K 31/282; A61K 33/243; A61K 9/0078; A61P 35/04; A61P 35/00; A61P 11/00
See application file for complete search history.

(56) References Cited

U.S. PATENT DOCUMENTS

| 3,993,754 A | 11/1976 | Rahman et al. |
| 4,105,027 A | 8/1978 | Lundquist |
| 4,145,410 A | 3/1979 | Sears |
| 4,192,309 A | 3/1980 | Poulsen |
| 4,224,179 A | 9/1980 | Schneider |
| 4,227,522 A | 10/1980 | Carris |
| 4,235,871 A | 11/1980 | Papahadjopoulos et al. |
| 4,451,447 A | 5/1984 | Kaplan et al. |
| 4,522,803 A | 6/1985 | Lenk et al. |
| 4,529,561 A | 7/1985 | Hunt et al. |
| 4,572,425 A | 2/1986 | Russell |
| 4,588,578 A | 5/1986 | Fountain et al. |
| 4,590,001 A | 5/1986 | Stjernholm |
| 4,627,432 A | 12/1986 | Newell et al. |
| 4,721,612 A | 1/1988 | Janoff et al. |
| 4,767,874 A | 8/1988 | Shima et al. |
| 4,778,054 A | 10/1988 | Newell et al. |
| 4,811,731 A | 3/1989 | Newell et al. |
| RE33,071 E | 9/1989 | Stjernholm |
| 4,889,724 A | 12/1989 | Kasan et al. |
| 4,975,282 A | 12/1990 | Cullis et al. |
| 4,981,692 A | 1/1991 | Popescu et al. |
| 5,008,050 A | 4/1991 | Cullis et al. |
| 5,013,556 A | 5/1991 | Woodie et al. |
| 5,019,369 A | 5/1991 | Presant et al. |
| 5,030,453 A | 7/1991 | Lenk et al. |
| 5,035,237 A | 7/1991 | Newell et al. |
| 5,049,388 A | 9/1991 | Knight et al. |
| 5,059,421 A | 10/1991 | Loughrey et al. |
| 5,077,056 A | 12/1991 | Bally et al. |
| 5,077,057 A | 12/1991 | Szoka, Jr. |
| 5,094,854 A | 3/1992 | Ogawa et al. |
| 5,117,022 A | 5/1992 | Khokhar et al. |
| 5,141,751 A | 8/1992 | Tomikawa et al. |
| 5,169,637 A | 12/1992 | Lenk et al. |
| 5,186,940 A | 2/1993 | Khokhar et al. |
| 5,225,212 A | 7/1993 | Martin et al. |
| 5,264,221 A | 11/1993 | Tagawa et al. |
| 5,320,906 A | 6/1994 | Eley et al. |
| 5,567,434 A | 10/1996 | Szoka, Jr. |
| 5,616,334 A | 4/1997 | Janoff et al. |
| 5,641,662 A | 6/1997 | Debs et al. |
| 5,665,383 A | 9/1997 | Grinstaff et al. |

(Continued)

FOREIGN PATENT DOCUMENTS

| CN | 1088777 A | 7/1994 |
| CN | 1976711 A | 6/2007 |

(Continued)

OTHER PUBLICATIONS

Chou (Phase Ib/IIa study of sustained release lipid inhalation targeting cisplatin, Journal of Clinical Oncology, 2007 ASCO Annual Meeting Proceedings (Post-Meeting Edition), vol. 25, No. 18S (Jun. 20 Supplement), 2007: 9525)—Accessed from http://meeting.ascopubs.org/cgi/content/short/25/18_suppl/9525 on Dec. 29, 2015.*
Limmahakhun (Relationships between Serum Biomarker Levels and Clinical Presentation of Human Osteosarcomas, Asia Pacific Journal of Cancer Prevention (vol. 12, No. 7, 2011)—accessed from http://www.apocpcontrol.org/page/apjcp_issues_view.php?sid=Entrez:PubMed&id=pmid:22126551&key=2011.12.7.1717 on Dec. 29, 2015.*
International Search Report and Written Opinion for International Application No. PCT/US2006/043159, dated May 8, 2007, 5 pages.
Supplementary European Search Report for European Application No. 13836095.3, dated Jun. 2, 2016, 11 pages.
International Search Report and Written Opinion for International Application No. PCT/US2013/058025, dated Jan. 10, 2014, 13 pages.

(Continued)

Primary Examiner — Gollamudi S Kishore
(74) Attorney, Agent, or Firm — Cooley LLP

(57) ABSTRACT

The described invention provides methods for treating pulmonary cancer in a subject, by administering to the subject by inhalation a composition of inhalational lipid cisplatin (ILC) comprising a lipid-complexed cisplatin.

14 Claims, No Drawings

(56) References Cited

U.S. PATENT DOCUMENTS

| | | | |
|---|---|---|---|
| 5,756,353 A | 5/1998 | Debs | |
| 5,780,054 A | 7/1998 | Tardi et al. | |
| 5,795,589 A | 8/1998 | Mayer et al. | |
| 5,945,122 A | 8/1999 | Abra et al. | |
| 5,997,899 A | 12/1999 | Ye et al. | |
| 6,090,407 A | 7/2000 | Knight et al. | |
| 6,126,966 A | 10/2000 | Abra et al. | |
| 6,147,060 A | 11/2000 | Zasloff et al. | |
| 6,211,388 B1 | 4/2001 | Tsuji et al. | |
| 6,221,388 B1 | 4/2001 | Hersch et al. | |
| 6,274,115 B1 | 8/2001 | Presant et al. | |
| 6,352,996 B1 | 3/2002 | Cao et al. | |
| 6,419,901 B2 | 7/2002 | Placke et al. | |
| 6,440,393 B1 | 8/2002 | Waldrep et al. | |
| 6,451,784 B1 | 9/2002 | Placke et al. | |
| 6,511,676 B1 | 1/2003 | Boulikas | |
| 6,599,912 B1 | 7/2003 | Au et al. | |
| 6,669,958 B1 | 12/2003 | Trager et al. | |
| 6,723,338 B1 | 4/2004 | Sarris et al. | |
| 6,726,925 B1 | 4/2004 | Needham | |
| 6,787,132 B1 | 9/2004 | Gabizon et al. | |
| 6,793,912 B2 | 9/2004 | Pilkiewicz et al. | |
| 6,852,334 B1 | 2/2005 | Cullis et al. | |
| 6,921,527 B2 | 7/2005 | Platz et al. | |
| 7,025,988 B2 | 4/2006 | Zadi | |
| 7,063,860 B2 | 6/2006 | Chancellor et al. | |
| 7,544,369 B2 | 6/2009 | Boni et al. | |
| 9,107,824 B2 | 8/2015 | Pilkiewicz et al. | |
| 2001/0010822 A1 | 8/2001 | Cherian | |
| 2002/0009415 A1 | 1/2002 | Batich et al. | |
| 2002/0012998 A1 | 1/2002 | Gonda et al. | |
| 2002/0110586 A1 | 8/2002 | Madden et al. | |
| 2002/0182248 A1 | 12/2002 | Yamauchi et al. | |
| 2002/0187105 A1 | 12/2002 | Zou et al. | |
| 2003/0017210 A1 | 1/2003 | Debregeas et al. | |
| 2003/0059375 A1 | 3/2003 | Perez-Soler et al. | |
| 2003/0059402 A1 | 3/2003 | Jin et al. | |
| 2003/0099718 A1 | 5/2003 | Burrell et al. | |
| 2003/0185879 A1 | 10/2003 | Boulikas | |
| 2003/0224039 A1 | 12/2003 | Boni et al. | |
| 2004/0022842 A1 | 2/2004 | Eriguchi et al. | |
| 2004/0101553 A1 | 5/2004 | Lee et al. | |
| 2004/0156888 A1 | 8/2004 | Jensen et al. | |
| 2004/0170678 A1 | 9/2004 | Madden et al. | |
| 2005/0037341 A1 | 2/2005 | Dierynck et al. | |
| 2005/0074499 A1 | 4/2005 | Tagawa et al. | |
| 2005/0107287 A1 | 5/2005 | Pilkiewicz et al. | |
| 2005/0207987 A1 | 9/2005 | Speirs et al. | |
| 2005/0238705 A1 | 10/2005 | Hu et al. | |
| 2005/0249822 A1 | 11/2005 | Pilkiewicz et al. | |
| 2006/0159712 A1 | 7/2006 | Lee et al. | |
| 2006/0246124 A1 | 11/2006 | Pilkiewicz et al. | |
| 2007/0065522 A1 | 3/2007 | Pilkiewicz et al. | |
| 2007/0122350 A1 | 5/2007 | Pilkiewicz et al. | |
| 2007/0190182 A1 | 8/2007 | Pilkiewicz et al. | |
| 2008/0187578 A1 | 8/2008 | Lee et al. | |
| 2009/0130193 A1 | 5/2009 | Pilkiewicz et al. | |
| 2009/0130194 A1* | 5/2009 | Pilkiewicz | A61K 9/0019 424/450 |
| 2009/0202431 A1 | 8/2009 | Gibbs et al. | |
| 2010/0098665 A1* | 4/2010 | Leonard | A61P 35/00 424/93.2 |
| 2012/0027727 A1* | 2/2012 | Hall | A61P 35/00 424/93.2 |
| 2012/0121513 A1* | 5/2012 | Frank | A61P 21/04 424/9.2 |
| 2016/0166608 A1 | 6/2016 | Pilkiewicz et al. | |

FOREIGN PATENT DOCUMENTS

| | | |
|---|---|---|
| EP | 0551169 | 7/1993 |
| EP | 0719546 | 7/1996 |
| EP | 1369132 | 12/2003 |
| JP | H05-255070 | 10/1993 |
| JP | 2001-501173 | 1/2001 |
| JP | 2003-277272 | 10/2003 |
| JP | 2004-010481 | 1/2004 |
| WO | WO 85/00968 | 3/1985 |
| WO | WO 86/01102 | 2/1986 |
| WO | WO 87/02219 | 4/1987 |
| WO | WO 89/00846 | 2/1989 |
| WO | WO 91/16038 | 10/1991 |
| WO | WO 95/28948 | 11/1995 |
| WO | WO 98/07409 | 2/1998 |
| WO | WO 98/24425 | 6/1998 |
| WO | WO 98/29110 | 7/1998 |
| WO | WO 98/33481 | 8/1998 |
| WO | WO 99/15153 | 4/1999 |
| WO | WO 2000/027359 | 5/2000 |
| WO | WO 2001/032139 | 5/2001 |
| WO | WO 2001/034130 | 5/2001 |
| WO | WO 2001/082892 | 11/2001 |
| WO | WO 2003/015521 | 2/2003 |
| WO | WO 2003/015707 | 2/2003 |
| WO | WO 2004/047802 | 6/2004 |
| WO | WO 2004/054499 | 7/2004 |
| WO | WO 2005/037341 | 4/2005 |
| WO | WO 2005/089448 | 9/2005 |
| WO | WO 2005/112957 | 12/2005 |
| WO | WO 2006/055352 | 5/2006 |
| WO | WO 2007/056264 | 5/2007 |
| WO | WO 2007/099377 | 9/2007 |
| WO | WO 2008/022189 | 2/2008 |
| WO | WO 2009/100330 | 8/2009 |
| WO | WO 2011/103591 | 8/2011 |
| WO | WO 2014/039533 | 3/2014 |

OTHER PUBLICATIONS

Adhikari, A. S. et al., "CD117 and Stro-1 identify osteosarcoma tumor-initiating cells associated with metastasis and drug resistance," Cancer Research, 70(11):4602-2612 (May 2010).

Alberts, D. S. et al., "Intraperitoneal cisplatin plus intravenous cyclophosphamide versus intravenous cisplatin plus intravenous cyclophosphamide for stage III ovarian cancer," New England Journal of Medicine, 335(26):1950-1955 (1996).

Alderden, R. A. et al., "The discovery and development of cisplatin," Journal of Chemical Education, 83(5):728-734 (2006).

Allen, T. M. et al., "Liposomal drug delivery systems: From concept to clinical applications," Advanced Drug Delivery Reviews, 65:36-48 (2013).

Allison, D. C. et al., "A Meta-Analysis of Osteosarcoma Outcomes in the Modern Medical Era," Sarcoma, vol. 2012, Article ID 704872 (2012), 10 pages.

Ando, K. et al., "Current Therapeutic Strategies and Novel Approaches in Osteosarcoma," Cancers, 5:591-616 (2013).

Bacci, G. et al., "Osteogenic Sarcoma of the Extremity with Detectable Lung Metastases at Presentation. Results of Treatment of 23 Patients with Chemotherapy followed by Simultaneous Resection of Primary and Metastatic Lesions," Cancer, 79(2):245-254 (1997).

Bacci, G. et al., "Treatment and outcome of recurrent osteosarcoma: Experience at Rizzoli in 235 patients initially treated with neoadjuvant chemotherapy," Acta Oncologica, 44:748-755 (2005).

Bally, M. B. et al., "Novel procedures for generating and loading liposomal systems," In: Liposomes as Drug Carriers, Gregoriadis, G. (ed.), John Wiley & Sons Ltd., 13 pages (1988).

Bangham, A. D. et al., "Diffusion of Univalent Ions across the Lamellae of Swollen Phospholipids," J. Mol. Biol., 13:238-252 (1965).

Banno, B. et al., "The functional roles of poly(ethylene glycol)-lipid and lysolipid in the drug retention and release from lysolipid-containing thermosensitive liposomes in vitro and in vivo," Journal of Pharmaceutical Science, 99(5):2295-2308 (2010).

Barnham, K. J. et al., "Ring-Opened Adducts of the Anticancer Drug Carboplatin with Sulfur Amino Acids," Inorg. Chem., 35(4):1065-1072 (1996).

(56) References Cited

OTHER PUBLICATIONS

Bates, S. R. et al., "Phospholipids co-isolated with rat surfactant protein C account for the apparent protein-enhanced uptake of liposomes into lung granular pneumocytes," Exp. Lung Res., 15(5):695-708 (1989).
Baum, E. S. et al., "Phase II trial of cisplatin in refractory childhood cancer: Children's cancer study group report," Cancer Treat. Rep., 65:815-822 (1981).
Bell, J. H. et al., "Dry powder aerosols I: A new powder inhalation device," J. Pharm. Sci., 60(10):1559-1564 (1971).
Bellmann, R. et al., "Differences in pharmacokinetics of amphotericin B lipid formulations despite clinical equivalence," Clinical Infection Diseases, 36:1500-1501 (2003).
Berek, J. S. et al., "Intraperitoneal administration of biologic agents," Int. J. Gynecol. Cancer, 1:26-29 (1992).
Bielack, S. S. et al., "Second and Subsequent Recurrences of Osteosarcoma: Presentation, Treatment, and Outcomes of 249 Consecutive Cooperative Osteosarcoma Study Group Patients," Journal of Clinical Oncology, 27(4):557-565 (2009).
Bielack, S. et al., "Osteosarcoma: ESMO Clinical Recommendations for diagnosis, treatment and follow-up," Annals of Oncology, 20(4):iv137-iv139 (2009).
Borch, R. F. et al., "Inhibition of cis-platinum nephrotoxicity by diethyldithiocarbamate rescue in a rat model," Proc. Natl. Acad. Sci USA, 76(12):6611-6614 (1979).
Boulikas, T., "Low toxicity and anticancer activity of a novel liposomal cisplatin (Lipoplatin) in mouse xenografts," Oncology Reports, 12(1):3-12 (2004).
Breathnach, O. S. et al., "Clinical Features of Patients with Stage IIIB and IV Bronchioloalveolar Carcinoma of the Lung," Cancer, 86(7):1165-1173 (1999).
Briccoli, A. et al., "Resection of Recurrent Pulmonary Metastases in Patients with Osteosarcoma," Cancer, 104:1721-1725 (2005).
Brock, P. R. et al., "Cisplatin ototoxicity in children: A practical grading system," Med. Pediatr. Oncol., 19(4):295-300 (1991).
Burger, K. N. J. et al., "Nanocapsules: lipid-coated aggregates of cisplatin with high cytotoxicity," Nature Medicine, 8(1):81-84 (2002).
Cascales, L., "A study by molecular dynamics simulation of the effect of the ionic strength on the properties of a model DPPC/DPPS asymmetric membrane," The Journal of the Argentine Chemical Society, 94(1/3):157-168 (2006).
Chang, H-J et al., "Clinical development of liposome-based drugs: formulation, characterization, and therapeutic efficacy," International Journal of Nanomedicine, 7:49-60 (2012).
Chapman, D. et al., "Physicochemical Properties of Phospholipids and Lipid-Water Systems," Chapter 1 In: Liposome Technology, vol. I, Preparation of Liposomes, Gregoriadis, G. (ed.), CPC Press, Inc., Boca Raton, Florida, 21 pages (1968).
Chi, K. H. et al., "Elimination of dose limiting toxicities of cisplatin, 5-fluorouracil, and leucovorin using a weekly 24-hour infusion schedule for the treatment of patients with nasopharyngeal carcinoma," Cancer, 76(11):2186-2192 (1995).
Chiu, S. W. et al., "Structure of sphingomyelin bilayers: a simulation study," Biophysical Journal, 85:3624-3635 (2003).
Chou, A. J. et al., "Chemotherapy resistance in osteosarcoma: Current challenges and future directions," Expert Rev. Anticancer Ther., 6(7):1075-1085 (2006).
Chou, A. J. et al., "Inhaled lipid cisplatin (ILC) in the treatment of patients with relapsed/progressive osteosarcoma metastatic to the lung," Pediatr. Blood Cancer, 60(4):580-586 (Apr. 2013).
Cisplatin Injection, Drug Information Label, Jun. 2004, 15 pages.
Cohen, G. L. et al., "Sequence dependent binding of cis-dichlorodiammineplatinum(II) to DNA," J. Am. Chem. Soc., 102(7):2487-2488 (1980).
Comis, R. L., "Carboplatin in the treatment of non-small cell lung cancer: A review," Oncology, 50(2):37-41 (1993).
Coventry, M. B. et al., "Osteogenic sarcoma," Journal of Bone and Joint Surgery, 39-A(4):741-758 (1957).
Dabkowska, A. P. et al., "The effect of neutral helper lipids on the structure of cationic lipid monolayers," Journal of the Royal Society Interface, Published online Aug. 10, 2011, <URL: http://rsif.royalsocietypublishing.org>, 15 pages.
Dai, X. et al., "Review of therapeutic strategies for osteosarcoma, chondrosarcoma, and Ewing's sarcoma," Med. Sci. Moni., 17(8):RA177-RA190 (2011).
Deamer, D. W. et al., "Chapter 1—Liposome Preparation: Methods and Mechanisms," In Liposomes, Ostro, M. (ed.), Marcel Dekker, Inc., New York, 27 pages (1983).
DeConti, R. C. et al., "Clinical and pharmacological studies with cis-Diamminedichloroplatinum(II)[1]," Cancer Research, 33:1310-1315 (1973).
Dedrick, R. L. et al., "Pharmacokinetic rationale for peritoneal drug administration in the treatment of ovarian cancer," Cancer Treat. Rep., 62(1):1-9 (1978).
Demayo, F. et al., "Mesenchymal-epithelial interactions in lung development and repair: are modeling and remodeling the same process?," Am. J. Physiol. Lung Cell Mol. Physiol., 283:L510-L517 (2002).
Devarajan, P. et al., "Low renal toxicity of lipoplatin compared to cisplatin in animals," Anticancer Research, 24:2193-2200 (2004).
Dolman, R. C. et al., "Studies of the binding of a series of platinum(IV) complexes to plasma proteins," J. Inorg. Biochem., 88:260-267 (2002).
Embree, L. et al., "Chromatographic Analysis and Pharmacokinetics of Liposome-Encapsulated Doxorubicin in Non-Small-Cell Lung Cancer Patients," Journal of Pharmaceutical Sciences, 82(6):627-634 (1993).
Enneking, W. F. et al., "A System for the Surgical Staging of Musculoskeletal Sarcoma," Clin. Orthop. Relat. Res., 153:106-120 (1980).
Ferguson, W. S. et al., "Presurgical window of carboplatin and surgery and multidrug chemotherapy for the treatment of newly diagnosed metastatic or unresectable osteosarcoma: pediatric oncology group trial," J. Pediatr. Hematol. Oncol., 23(6):340-348 (2001).
Ferrari, S. et al., "Postrelapse survival in osteosarcoma of the extremities: prognostic factors for long-term survival," J. Clin. Oncol., 21(4):710-715 (2003).
Freise, J. et al., "Pharmacokinetics of liposome-encapsulated cisplatin in rats," Arch. Int. Pharmacodyn. Ther., 258(2):180-192 (1982).
Fuertes, M. A. et al., "Novel concepts in the development of platinum antitumor drugs," Curr. Med. Chem.—Anti-Cancer Agents, 2(4):539-551 (2002).
Fujita, J. et al., "Respiratory failure due to pulmonary lymphangitis carcinomatosis," Chest, 103(3):967-968 (1993).
Gately, D. P. et al., "Cellular accumulation of the anticancer agent cisplatin: A review," Br. J. Cancer, 67:1171-1176 (1993).
Geiger, K. et al., "Cellular distribution and clearance of aerosolized dipalmitoyl lecithin," J. Appl. Physiol., 39(5)759-766 (1975).
Gondal, J. A. et al., "Comparative pharmacological, toxicological and antitumoral evaluation of free and liposomeencapsulated cisplatin in rodents," Eur. J. Cancer, 29A(11):1536-1542 (1993).
Gonzalez-Rothi, R. J. et al., "Liposomes and pulmonary alveolar macrophages: functional and morphologic interactions," Exp. Lung Res., 17:687-705 (1991).
Goorin, A. M. et al., "Phase II/III trial of etoposide and high-dose ifosfamide in newly diagnosed metastatic osteosarcoma: A pediatric oncology group trial," J. Clin. Oncol., 20(2):426-433 (2002).
Gorlick, R., "Current concepts on the molecular biology of osteosarcoma," In: Pediatric and Adolescent Osteosarcoma, Jaffe, N. et al. (eds.), Cancer Treatment and Research, 152:467-478 (2010).
Gregoriadis, G., "Targeting of drugs: Implications in medicine," Lancet, 2:241-247 (1981).
Hambley, T. W., "Platinum binding to DNA: structural controls and consequences," J. Chem. Soc., Dalton Trans., 2711-2718 (2001).
Harris, M. B. et al., "Treatment of metastatic osteosarcoma at diagnosis: A pediatric oncology group study," J. Clin. Oncol., 16(11):3641-3648 (1998).
Harting, M. T. et al., "Management of osteosarcoma pulmonary metastases," Semin. Pediatr. Surg., 15(1):25-29 (2006).
Hayes, F. A. et al., "Tetany: A complication of cis-dichlorodiammineplatinum(II) therapy," Cancer Treatment Reports, 63(4):547-548 (1979).

(56) References Cited

OTHER PUBLICATIONS

Hickey, A. J. et al., "A new millennium for inhaler technology," Pharmaceutical Technology, pp. 116-125 (Jun. 1997).
Ho, C. et al., "Hydration and order in lipid bilayers," Biochemistry, 34(18):6188-6195 (1995).
Hoffman, P. C. et al., "Lung Cancer," The Lancet, 355:479-485 (2000).
Hojo, K. et al., "A case of adenocarcinoma of lung cancer with multiple brain metastasis and lymphangitis carcinomatosa responding well to chemotherapy with carboplatin, etoposide and ifosfamide," Jpn. J. Cancer Chemother., 19(14):2403-2406 (1992) (with English Summary).
Ishida, S. et al., "Uptake of the anticancer drug cisplatin mediated by the copper transporter Ctr1 in yeast and mammals," PNAS, 99(22):14298-14302 (2002).
Ivanov, A. I. et al., "Cisplatin Binding Sites on Human Albumin," J. Biol. Chem., 273:14721-14730 (1998).
Jaffe, N. et al., "Can Cure in Patients with Osteosarcoma Be Achieved Exclusively with Chemotherapy and Abrogation of Surgery?," Cancer, 95(10):2202-2210 (2002).
Jahnig, F., "Structural order of lipids and proteins in membranes: evaluation of fluorescence anisotropy data," Proc. Natl. Acad. Sci. USA, 76(12):6361-6365 (1979).
Jamieson, E. R. et al., "Structure, recognition, and processing of cisplatin-DNA adducts," Chem. Rev., 99(9):2467-2498 (1999).
Kelland, L. R., "Preclinical perspectives on platinum resistance," Drugs, 59(4):1-8 (2000).
Kelland, L., "The resurgance of platinum-based cancer chemotherapy," Nature Reviews, 7:573-584 (2007).
Kempf-Bielack, B. et al., "Osteosarcoma relapse after combined modality therapy: An analysis of unselected patients in the cooperative osteosarcoma study group (COSS)," J. Clin. Oncol., 23(3):559-568 (2005).
Kinoshita, A., "Investigation of cisplatin inhalation chemotherapy effects on mice after air passage implantation of FM3A cells," Journal of Japan Society for Cancer Therapy, 28(4):705-715 (1993).
Knight, V. et al., "Anti-Cancer Activity of 9-Nitrocamptothecin Liposome Aerosol in Mice," Transactions of the American Clinical and Climatological Association, 111:135-145 (2000).
Koshkina, N. V. et al., "9-Nitrocamptothecin Liposome Aerosol Treatment of Melanoma and Osteosarcoma Lunq Metastases in Mice," Clinical Cancer Research, 6(7):2876-2880 (2000).
Lansky, S. B. et al., "The measurement of performance in childhood cancer patients," Cancer, 60(7):1651-1656 (1987).
Lee, D. S. et al., "Predicting survival in patients with advanced non-squamous non-small cell lung cancer: Validating the extent of metastasis," Cancer Res. Treat., 45(2):95-102 (2013).
Leekumjorn, S. et al., "Molecular simulation study of structural and dynamic properties of mixed DPPC/DPPE bilayers," Biophysical Journal, 90(11):3951-3965 (2006).
Lehninger, A. L. et al., Principles of Biochemistry, Worth Publishers: New York, pp. 111-114, 134-135, 137, 240-245, 247, 249-252, 254, 256-259 and 262 (1993).
Leighl, N. B. et al., "A phase I study of pegylated liposomal doxorubicin hydrochloride (CaelyxTM) in combination with cyclophosphamide and vincristine as second-line treatment of patients with small-cell lung cancer," Clinical Lung Cancer, 5(2):107-112 (2003).
Lempers, E. L. M. et al., "Interactions of platinum amine compounds with sulfur-containing biomolecules and DNA fragments," Adv. Inorg. Chem. 37:175-217 (1991).
Leserman, L. et al., "Ligand Targeting of Liposomes," In: Liposomes—From Biophysics to Therapeutics, pp. 157-194, Ostro, M. (ed.), New York, NY, Marcel Dekker (1987).
Lewis, R. E. et al., "Comparative analysis of amphotericin B lipid complex and liposomal amphoterin B kinetics of lung accumulation and fungal clearance in a murine model of acute invasive pulmonary aspergillosis," Antimicrobial Agents and Chemotherapy, 51(4):1253-1258 (2007).

Lewis, R. E. et al., "Comparative pharmacodynamics of amphotericin B lipid complex and liposomal amphoterin B in a murine model of pulmonary mucormycosis," Antimicrobial Agents and Chemotherapy, 54(3):1298-1304 (2010).
Li, X-M et al., "Sphingomyelin interfacial behavior: The impact of changing acyl chain composition," Biophysical Journal, 78:1921-1931 (2000).
Liu, D. et al., "Application of liposomal technologies for delivery of platinum analogs in oncology," International Journal of Nanomedicine, 8:3309-3319 (2013).
Lloyd, P. et al., "A new unit dose, breath actuated aerosol drug delivery system," In: Respiratory Drug Delivery V, Program and Proceedings, Dalby, R. N. (eds.), Interpharm Press, Buffalo Grove, IL, pp. 364-366 (1996).
Loberg, R. D. et al., "Enhanced Glycogen Synthase Kinase-3 Activity Mediates Hypoxia-induced Apoptosis of Vascular Smooth Muscle Cells and Is Prevented by Glucose Transport and Metabolism," J. Biol. Chem., 277(44):41667-41673 (2002).
Lopez-Berestein, G. et al., "Liposomal amphotericin B for the treatment of systemic fungal infections in patients with cancer: A preliminary study," J. Infect. Dis., 151(4):704-710 (1985).
Markman, M., "Intraperitoneal therapy of ovarian cancer," The Oncologist, 1:18-21 (1996).
Markman, M., "Intraperitoneal antineoplastic agents for tumors principally confined to the peritoneal cavity," Cancer Treatment Reviews, 13(4):219-242 (1986).
Markman, M., "Intraperitoneal chemotherapy," Semin. Oncol., 18(3):248-254 (1991).
Markman, M. et al., "Responses to second-line cisplatin-based intraperitoneal therapy in ovarian cancer: Influence of a prior response to intravenous cisplatin," J. Clin. Oncol., 9(10):1801-1805 (1991).
Maurer, N. et al., "Developments in liposomal drug delivery systems," Expert Opin. Biol. Ther., 1(6):923-947 (2001).
Mayer, L. D. et al. "Techniques for encapsulating bioactive agents into liposomes," Chemistry and Physics of Lipids, 40:333-345 (1986).
Merimsky, O. et al., "Palliative treatment for advanced or metastatic osteosarcoma," IMAJ, 6:34-38 (2004).
Meyers, P. A. et al., "Osteosarcoma," Pediatr. Clin. North Am., 44(4):973-989 (1997).
Meyers, P. A. et al., "Osteogenic sarcoma with clinically detectable metastasis at initial presentation," J. Clin. Oncol., 11(3):449-453 (1993).
Mills, J. K. et al., "Lysolipid incorporation in dipalmitoylphosphatidylcholine bilayer membranes enhances the ion permeability and drug release rates at the membrane phase transition," Biochimica et Biophysica Acta, 1716:77-96 (2005).
Mizumura, Y. et al., "Cisplatin-incorporated Polymeric Micelles Eliminate Nephrotoxicity, While Maintaining Antitumor Activity," Jpn. J. Cancer Res., 92:328-336 (2001).
Mohseny, A. B. et al., "Osteosarcoma originates from mesenchymal stem cells in consequence of aneuploidization and genomic loss of Cdkn2," J. Pathol., 219(3):294-305 (2009).
Needham, D. et al., "A new temperature-sensitive liposome for use with mild hyperthermia: characterization and testing in a human tumor xenograft model," Cancer Research, 60(5):1197-1201 (2000).
Nelson, D. L., Lehninger Principles of Biochemistry, 3rd Edition, Worth Publishers, pp. 364-365, 390, 392-393 (2000).
Nelson, G. J., "Composition of neutral lipids from erythrocytes of common mammals," Journal of Lipid Research, 8:374-379 (1967).
Oken, M. M. et al., "Toxicity and response criteria of the Eastern Cooperative Oncology Group," Am. J. Clin. Oncol., 5:649-655 (1982).
Okuyuma, S. et al., "Reinforcing aerosol cisplatin for radiotherapy of laryngeal cancer," Tohoku Journal of Experimental Medicine, 169(3):253-255 (1993).
Ouyang, L. et al., "A three-plasma miRNA signature serves as novel biomarkers for osteosarcoma," Medical Oncology, 30(1):340 (2013); Published online: Dec. 27, 2012, 7 pages.
Pandit, S. A. et al., "Sphingomyelin-cholesterol domains in phospholipid membranes: atomistic simulation," Biophysical Journal, 87:1092-1100 (2004).

(56) References Cited

OTHER PUBLICATIONS

Papahadjopoulos, D. et al., "Phospholipid model membranes. I. Structural characteristics of hydrated liquid crystals," Biochimica et Biophysica Acta., 135:624-638 (1967).
Parry-Billings, M. et al., "Design, development and performance of a novel multidose dry-powder inhaler," Pharmaceutical Technology, pp. 24-34 (Nov. 1999) (previously appeared in Pharmaceutical Technology, 23:70-82 (Oct. 1999).
Perez-Soler, R. et al., "Toxicity and antitumor activity of cis-Bis-cyclopentenecarboxylato-1,2-diaminocyclohexane Platinum(II) encapsulated in multilamellar vesicles," Cancer Research, 46(12):6269-6273 (1986).
Platinoi®-AQ (cisplatin injection), Drug Information Label (1999).
Possmayer, F. et al., "The pulmonary surfactant: Control of fluidity at the air-liquid interface," In: Membrane Fluidity, Kates M. et al. (eds.), pp. 57-67, Clifton, NJ, Humana Press (1980).
Potkul, R. K. et al., "Toxicities in rats with free versus liposomal encapsulated cisplatin," Am. J. Obstet. Gynecol., 164(2):652-658 (1991).
Prestayko, A. W. et al., "Cisplatin (cis-diamminedichloroplatinum II)," Cancer Treatment Reviews, 6(1):17-39 (1979).
Rahman, A. et al., "Liposomal protection of adriamycin-induced cardiotoxicity in mice[1]," Cancer Research, 40:1532-1537 (1980).
Richardson, V. J. et al., "Tissue distribution and tumour localization of 99m-technetium-labelled liposomes in cancer patients," Br. J. Cancer, 40:35-43 (1979).
Ritter, J. et al., "Osteosarcoma," Annals of Oncology, 21(7):vii320-vii325 (2010).
Rowinsky, E. K. et al., "Paclitaxel (Taxol)," N. Engl. J. Med., Review Article, 332(15):1004-1014 (1995).
Ryman, B. E. et al., "Liposomes—Further Considerations of their Possible Role as Carriers of Therapeutic Agents," Targeting of Drugs, Gregoriadis, G. et al. (eds.), Plenum Press, New York, pp. 235-248 (1982).
Schiller, J. H. et al., "Current standards of care in small-cell and non-small-cell lung cancer," Oncology, 61(1):3-13 (2001).
Schwartsmann, G. et al., "A phase I trial of cisplatin plus decitabine, a new DNA-hypomethylating agent, in patients with advanced solid tumors and a follow-up early phase II evaluation in patients with inoperable nonsmall cell lung cancer," Investigational New Drugs, 18(1):83-91 (2000).
Seki, K. et al., "Cisplatin (CDDP) specifically induces apoptosis via sequential activation of caspase-8, -3 and -6 in osteosarcoma," Cancer Chemother. Pharmacol., 45:199-206 (2000).
Shek, P. N. et al., "Liposomes: a new generation of drug and vaccine carriers," Mod. Med. Canada, 41(4):314-326 (1986).
Smondyrev, A. M. et al., "Structure of dipalmitoylphosphatidylcholine/cho esterol bilayer at low and high cholesterol concentrations: Molecular dynamics simulation," Biophysical Journal, 77:2075-2089 (1999).
Stathopoulos, G. P. et al., "Paclitaxel combined with cis-platin as second-line treatment in patients with advanced non-small cell lung cancers refractory to cis-platin," Oncology Reports, 6:797-800 (1999).
Stathopoulos, G. P. et al., "Pharmacokinetics and adverse reactions of a new liposomal cisplatin (Lipoplatin): Phase I study," Oncology Reports, 13:589-595 (2005).

Steerenberg, P. A. et al., "Liposomes as drug carrier system for cis-diamminedichloroplatinum (II). II. Antitumor activity in vivo, induction of drug resistance, nephrotoxicity and Pt distribution," Cancer Chemother. Pharmacol., 21(4):299-307(1988).
Steerenberg, P. A. et al., "Liposomes as a drug carrier system for cis-diamminedichloroplatinum (II). I. Binding capacity, stability and tumor cell growth inhibition in vitro," International Journal of Pharmaceutics, 40:51-62 (1987).
Sur, B. et al., "Effect of liposomal encapsulation of cis-platinum diamminodichloride in the treatment of ehrlich ascites carcinoma," Oncology, 40(5):372-376 (1983).
Szoka, F., Jr. et al., "Comparative properties and methods of preparation of lipid vesicles (Liposomes)," Ann. Rev. Biophys. Bioeng., 9:467-508 (1980).
Tom, J. W. et al., "Particle formation with supercritical fluids—A review," Journal of Aerosol Science, 22(5):555-584 (1991).
Vadiei, K. et al., "Pharmacokinetics of liposome-entrapped cis-bis-neodecanoato-trans-R,R-1,2-diaminocyclohexane platinum(II) and cisplatin given i.v. and i.p. in the rat," Cancer Chemotherapy and Pharmacology, 30(5):365-369 (1992).
Yokes, E. E. et al., "A phase 1 study of STEALTH cisplatin (SPI-77) and vinorelbine in patients with advanced non-small-cell lung cancer," Clinical Lung Cancer, 2(2):128-132 (2000).
Wang, S. et al., "Feasibility and long-term efficacy of video-assisted thoracic surgery for unexpected pathologic N2 disease in non-small cell lung cancer," Ann. Thorac. Med., 8(3):170-175 (2013).
Ward, W. G. et al., "Pulmonary metastases of stage IIB extremity osteosarcoma and subsequent pulmonary metastases," J. Clin. Oncol., 12(9):1849-1858 (1994).
Weiss, R. B. et al., "New cisplatin analogues in development. A review," Drugs, 46(3):360-377 (1993).
Wittgen, B. P. H. et al., "Assessing a system to capture stray aerosol during inhalation of nebulized liposomal cisplatin," Journal of Aerosol Medicine, 19(3):385-391 (2006).
Wittgen, B. P. H. et al., "Phase I study of aerosolized SLIT cisplatin in the treatment of patients with carcinoma of the lung," Clin. Cancer Res., 13(8):2414-2421 (2007).
Zhang, X. et al., "Periosteal stem cells are essential for bone revitalization and repair," J. Musculoskelet. Neuronal. Interact., 5(4):360-362 (2005).
Zhang, Y. et al., "The development of targeted therapy in small cell lung cancer," J. Thoracic Dis., 5(4):538-548 (2013).
Zou, Y. et al., "LB-268. Pharmacokinetics and organ distribution of liposomal cisplatin administered intravenously and intraperitoneally," Proceedings American Association Cancer Research (2005).
Eleison Pharmaceuticals LLC, "Phase 2 Study of Inhaled Lipid Cisplatin in Pulmonary Recurrent Osteosarcoma," ClinicalTrials.gov [online], NCT01650090, First Received on: Jul. 20, 2012, 5 pages.
Perkins, W. et al., (2005) "An Inhalation Formulation of Liposomal Cisplatin (SLITTM Cisplatin) for Treatment of Lung Cancer," Lipids, Liposomes & Biomembranes 2005: New Technologies, Jul. 26-30, University of British Columbia, Vancouver, Canada, p. 78.
Takahashi, T. et al., "Clinical study of pulmonary metastases from primary bone tumors," Haigan [Lung Cancer], 1972, vol. 12, No. 1, pp. 27-35 (with English Abstract).

* cited by examiner

PREVENTING PULMONARY RECURRENCE OF CANCER WITH LIPID-COMPLEXED CISPLATIN

CROSS-REFERENCE TO RELATED APPLICATION

This application claims the benefit of priority from U.S. provisional patent application Ser. No. 61/743,398, filed Sep. 4, 2012, the entire disclosure of which is incorporated herein by reference.

FIELD OF INVENTION

The described invention relates to methods and compositions for the treatment of pulmonary cancer.

BACKGROUND OF THE INVENTION

The Lung

Lung morphogenesis and repair are characterized by complex cell-cell interactions of endodermal and mesodermal origin, leading to (or returning to) an alveolar structure that can effectively exchange gases between the circulation and the alveolar space. During development, mesenchyme specifies both epithelial morphogenesis and differentiation, and the entire respiratory epithelium, from larynx to distal tips, exhibits a significant plasticity in its eventual phenotype that is dependent on the inductive cues it receives from the mesenchyme. DeMayo F, Am. J. Physiol. Lung Cell Mole. Physiol. 283: L510-L517 (2002). The inductive factors responsible for specification of distal lung epithelial phenotype are diffusible and active over a short distance, and control of lung epithelial growth and differentiation is multifactorial. Id.

During bronchial smooth muscle myogenesis in the embryonic lung (smooth muscle develops at sites that sustain mechanical tension), the process of cell elongation of peribronchial cells from round to elongated is promoted, at least in part, by the developing bronchial basement membrane. New epithelial-mesenchymal contacts produced during branching morphogensis stimulate the synthesis of laminin-alpha1 chain by both cell types. Id. Laminin-1, the main basement membrane constituent, is then produced and polymerizes at the epithelial-mesenchymal interface. Apposed mesenchymal cells use this polymer to spread and elongate, a process that triggers smooth muscle differentiation, which further stimulates myogenesis. Id.

Lung Cancer

Lung cancers, which generally start in the cells lining the bronchi and in other parts of the lung such as the bronchioles or alveoli, are thought to start as areas of pre-cancerous changes in the lung that first affect the DNA of these cells. Over time, the abnormal cells may acquire other gene changes, which cause them to progress to true cancer. As a cancer develops, the cancer cells may make angiogenic factors that cause new blood vessels to form nearby, thus nourishing the cancer cells, which can continue to grow and form a tumor large enough to be seen on imaging tests such as x-rays.

At some point, cells from the cancer may break away from the original tumor and spread (metastasize) to other parts of the body. Lung cancer is often a life-threatening disease because it tends to spread in this manner even before it can be detected on an imaging test such as a chest x-ray.

Types of Lung Cancer

There are two major types of lung cancer: (1) small cell lung cancer (SCLC); and (2) non-small cell lung cancer (NSCLC).

Small Cell Lung Cancer

About 10% to 15% of all lung cancers are small cell lung cancer (SCLC), named for the size of the cancer cells when seen under a microscope. Other names for SCLC are oat cell cancer, oat cell carcinoma, and small cell undifferentiated carcinoma.

SCLC often starts in the bronchi near the center of the chest. It is a highly aggressive neuroendocrine subtype of lung cancer usually with distal metastasis and very poor prognosis. Zhang, Y and He, J, J. Thoracic Dis. 5(4): 538-548 (2013).

Non-Small Cell Lung Cancer

About 85% to 90% of lung cancers are non-small cell lung cancer (NSCLC). There are 3 main subtypes of NSCLC: (1) adenocarcinoma; (2) squamous cell carcinoma; and (3) large cell carcinoma. Although the cells in these subtypes differ in their size, shape, and chemical make-up, they are grouped together because the approach to treatment and prognosis (outlook) are similar.

Other Types of Lung Cancer

Other tumors that can occur in the lungs include, for example, lung carcinoid tumors, adenoid cystic carcinomas, hamartomas, lymphomas and sarcomas and cancers that spread to the lungs (i.e., metastases).

Carcinoid tumors of the lung account for less than 5% of lung tumors. Most are slow-growing tumors that are called typical carcinoid tumors. They are generally cured by surgery. Some typical carcinoid tumors can spread, but they usually have a better prognosis (outlook) than small cell or non-small cell lung cancer. Atypical carcinoid tumors are less common. The outlook for these tumors is somewhere in between typical carcinoids and small cell lung cancer.

Other types of lung tumors, such as adenoid cystic carcinomas, hamartomas, lymphomas, and sarcomas, are rare and are treated differently from the more common lung cancers.

Cancers that start in other organs (such as the breast, pancreas, kidney, or skin) can sometimes spread (metastasize) to the lungs, but these are not lung cancers. For example, cancer that starts in the breast and spreads to the lungs is still breast cancer, not lung cancer. Treatment for metastatic cancer to the lungs is based on the primary cancer site.

Risk Factors for Lung Cancer

Tobacco smoke is by far the leading risk factor for lung cancer. At least 80% of lung cancer deaths are thought to result from smoking. Other risk factors include, for example, exposure to radon, asbestos, radioactive ores such as uranium, inhaled chemicals or minerals such as arsenic, beryllium, cadmium, silica, vinyl chloride, nickel compounds, chromium compounds, coal products, mustard gas, talc and talcum powder and chloromethyl ethers, air pollution, radiation therapy to the lungs, personal or family history of lung cancer, and certain dietary supplements.

Detection of Lung Cancer

Usually symptoms of lung cancer do not appear until the disease is already in an advanced, non-curable stage. Even when symptoms of lung cancer do appear, they may be mistaken for other problems, such as an infection or long-term effects from smoking, which may delay the diagnosis.

Some lung cancers are diagnosed early because they are found by accident as a result of tests for other medical conditions. For example, lung cancer may be found by imaging tests (such as a chest x-ray or chest CT scan), bronchoscopy (viewing the inside of lung airways through a flexible lighted tube), or sputum exam (microscopic examination of cells in coughed up phlegm) done for other reasons in patients with heart disease, pneumonia, or other lung conditions.

Common Signs and Symptoms of Lung Cancer

The most common symptoms of lung cancer include, for example, a cough that does not go away or gets worse, chest pain that is often worse with deep breathing, coughing, or laughing, hoarseness, weight loss and loss of appetite, coughing up blood or rust-colored sputum (spit or phlegm), shortness of breath, feeling tired or weak, infections such as bronchitis and pneumonia that don't go away or keep coming back, and new onset of wheezing.

When lung cancer spreads to distant organs, it may cause, for example, bone pain (like pain in the back or hips), neurologic changes (such as headache, weakness or numbness of an arm or leg, dizziness, balance problems, or seizures), jaundice (yellowing of the skin and eyes), and lumps near the surface of the body, due to cancer spreading to the skin or to lymph nodes (collections of immune system cells) in the neck or above the collarbone.

American Cancer Society's Guidelines for Lung Cancer Screening

The American Cancer Society has thoroughly reviewed the subject of lung cancer screening and issued the following guidelines that are aimed at doctors and other health care providers: patients should be asked about their smoking history. Patients who meet ALL of the following criteria may be candidates for lung cancer screening: (1) 55 to 74 years old; (2) in fairly good health; (3) have at least a 30 pack-year smoking history; and are either still smoking or have quit smoking within the last 15 years.

Imaging Tests

Chest X-Ray

This is often the first test performed to look for any masses or spots on the lungs. Plain x-rays of the chest can be done at imaging centers, hospitals, and doctors' offices.

Computed Tomography (CT) Scan

A CT (or CAT) scan, which is more likely to show lung tumors than routine chest x-rays, can also provide precise information about the size, shape, and position of any lung tumors and can help find enlarged lymph nodes that might contain cancer that has spread from the lung. This test can also be used to look for masses in the adrenal glands, liver, brain, and other internal organs that might be due to the spread of lung cancer.

The CT scan is a test that uses x-rays to produce detailed cross-sectional images of the body. A CT scanner takes many pictures as it rotates around the subject while the subject lies on a table. A computer then combines these pictures into images of slices of the part of the body being studied. Unlike a regular x-ray, a CT scan creates detailed images of the soft tissues in the body. Before a CT scan is performed, a contrast solution may be ingested or injected to help better outline structures in the body.

Magnetic Resonance Imaging (MRI) Scan

MRI scans are most often used to look for possible spread of lung cancer to the brain or spinal cord.

Like CT scans, MRI scans, which use radio waves and strong magnets instead of x-rays, provide detailed images of soft tissues in the body. The energy from the radio waves is absorbed and then released in a pattern formed by the type of body tissue and by certain diseases. A computer translates the pattern into a very detailed image of parts of the body. A contrast material (gadolinium) is often injected into a vein before the scan to better see details.

Positron Emission Tomography (PET) Scan

For PET scan imaging, fluorodeoxyglucose or FDG is injected into the blood. Because cancer cells in the body are growing rapidly, they absorb more of the radioactive FDG. A PET scanner then creates a picture of areas of radioactivity in the body. The picture is not finely detailed like a CT or MRI scan, but it provides helpful information about your whole body.

Bone Scan

A bone scan is useful to show if a cancer has spread to the bones.

For this test, a small amount of low-level radioactive material is injected into a vein (intravenously, or IV). The substance settles in areas of bone changes throughout the entire skeleton over the course of a few hours. A special camera detects the radioactivity and creates a picture of the skeleton. Areas of active bone changes attract the radioactivity and show up as "hot spots." These areas may suggest metastatic cancer, but arthritis or other bone diseases can also cause the same pattern. To distinguish among these conditions, other imaging tests such as plain x-rays or MRI scans may be used, or biopsy samples of the bone may be taken.

Diagnostic Tests

Symptoms and the results of certain tests may strongly suggest that a person has lung cancer, but the actual diagnosis of non-small cell lung cancer is made by looking at lung cells under a microscope.

The cells can be taken from lung secretions (sputum or phlegm), removed from a suspicious area (known as a biopsy), or found in fluid removed from the area around the lung (thoracentesis). The choice of which test(s) to use depends on the situation.

Sputum Cytology

A sample of sputum (mucus coughed up from the lungs) is looked at under a microscope to see if it contains cancer cells. The best way to do this is to get early morning samples 3 days in a row. This test is more likely to help find cancers that start in the major airways of the lung, such as most squamous cell lung cancers. It may not be as helpful for finding other types of non-small cell lung cancer.

Needle Biopsy

Doctors can often use a hollow needle to get a small sample from a suspicious area (mass). In a fine needle aspiration (FNA) biopsy, a doctor uses a syringe with a very thin, hollow needle (thinner than the ones used for blood tests) to withdraw (aspirate) cells and small fragments of tissue. In a core biopsy, a larger needle is used to remove one or more small cylinders (cores) of tissue. Core biopsies provide a larger sample than FNA biopsies.

While needle biopsies do not require a surgical incision, in some cases they might not provide enough of a sample to make a diagnosis and to classify DNA changes in the cancer cells that can aid in the selection of anticancer drugs.

If the suspected tumor is in the outer portion of the lungs, either kind of biopsy needle can be inserted through the skin on the chest wall. This is called a transthoracic needle biopsy. The area where the needle is to be inserted may be numbed with local anesthesia first. A doctor then guides the needle into the area while looking at the lungs with either fluoroscopy (where the image is shown on a screen rather than on film) or CT scans. Unlike fluoroscopy, CT doesn't give a constant picture, so the needle is inserted toward the mass, a CT image is taken, and the direction of the needle is guided based on the image. This is repeated a few times until the needle is within the mass.

A possible complication of this procedure is that air may leak out of the lung at the biopsy site and into the space between the lung and the chest wall, which can cause part of the lung to collapse and trouble breathing. This complication, called a pneumothorax, often gets better without any treatment. If not, it is treated by putting a small tube into the chest space and sucking out the air over a day or two, after which it usually heals on its own.

An FNA biopsy may also be done to check for cancer in the lymph nodes between the lungs. A transtracheal FNA or transbronchial FNA is done by passing the needle through the wall of the trachea (windpipe) or bronchi (the large airways leading into the lungs) during bronchoscopy or endobronchial ultrasound. In some cases an FNA biopsy is done during endoscopic esophageal ultrasound by passing the needle through the wall of the esophagus.

Bronchoscopy

Bronchoscopy can help detect some tumors or blockages in the larger airways of the lungs.

For this exam, a lighted, flexible fiber-optic tube (called a bronchoscope) is passed through the mouth or nose and down into the windpipe and bronchi. Small instruments can be passed down the bronchoscope to take biopsies (samples of tissue). The doctor can also sample cells from the lining of the airways with a small brush (bronchial brushing) or by rinsing the airways with sterile saltwater (bronchial washing). These tissue and cell samples are then examined under a microscope.

Endobronchial Ultrasound

Ultrasound is a type of imaging test that uses sound waves to create pictures of the inside of the body. For this test, a small, microphone-like instrument called a transducer gives off sound waves and picks up the echoes as they bounce off body tissues. The echoes are converted by a computer into a black and white image on a computer screen.

For endobronchial ultrasound, a bronchoscope is fitted with an ultrasound transducer at its tip and is passed down into the windpipe. This is done with local anesthesia and light sedation.

The transducer can be pointed in different directions to look at lymph nodes and other structures in the mediastinum (the area between the lungs). If suspicious areas such as enlarged lymph nodes are seen on the ultrasound, a hollow needle can be passed through the bronchoscope and guided into these areas to obtain a biopsy. The samples are then sent to a lab to be looked at under a microscope.

Endoscopic Esophageal Ultrasound

This test is like endobronchial ultrasound, except an endoscope (a lighted, flexible scope) is passed down the throat and into the esophagus (the tube connecting the throat to the stomach). This is done with local anesthesia and light sedation.

The esophagus lies just behind the windpipe and is close to some lymph nodes inside the chest to which lung cancer may spread. As with endobronchial ultrasound, the transducer can be pointed in different directions to look at lymph nodes and other structures inside the chest that might contain lung cancer. If enlarged lymph nodes are seen on the ultrasound, a hollow needle can be passed through the endoscope to get biopsy samples of them. The samples are then sent to a lab to be looked at under a microscope.

Mediastinoscopy and Mediastinotomy

These procedures may be done to look more directly at and get samples from the structures in the mediastinum (the area between the lungs).

A mediastinoscopy procedure is performed by making a small cut in the front of the neck and a thin, hollow, lighted tube is inserted behind the sternum (breast bone) and in front of the windpipe to look at the area. Instruments can be passed through this tube to take tissue samples from the lymph nodes along the windpipe and the major bronchial tube areas. Looking at the samples under a microscope can show whether cancer cells are present.

A mediastinotomy procedure is performed by making a slightly larger incision (usually about 2 inches long) between the left second and third ribs next to the breast bone. This lets the surgeon reach some lymph nodes that cannot be reached by mediastinoscopy.

Thoracentesis

If there is a buildup of fluid around the lungs (pleural effusion), doctors can use thoracentesis to determine if it was caused by cancer spreading to the lining of the lungs (pleura). The buildup might also be caused by other conditions, such as heart failure or an infection.

For this procedure, the skin is numbed and a hollow needle is inserted between the ribs to drain the fluid. (In a similar test called pericardiocentesis, fluid is removed from within the sac around the heart.) The fluid is checked under a microscope for cancer cells. Chemical tests of the fluid are also sometimes useful in telling a malignant (cancerous) pleural effusion from a benign (non-cancerous) one.

If a malignant pleural effusion has been diagnosed, thoracentesis may be repeated to remove more fluid. Fluid buildup can keep the lungs from filling with air, so thoracentesis can help the patient breathe better.

Thoracoscopy

Thoracoscopy can be performed to determine if cancer has spread to the spaces between the lungs and the chest wall, or to the linings of these spaces. It can also be used to sample tumors on the outer parts of the lungs as well as nearby lymph nodes and fluid, and to assess whether a tumor is growing into nearby tissues or organs. This procedure is not often done just to diagnose lung cancer, unless other tests such as needle biopsies are unable to get enough samples for the diagnosis.

A thoracoscopy is performed by making a small cut (incision) in the side of the chest wall. (Sometimes more than one cut is made.) A thin, lighted tube with a small video camera on the end is inserted through the incision to view the space between the lungs and the chest wall. Using this, a doctor can see potential cancer deposits on the lining of the lung or chest wall and remove small pieces of tissue to be looked at under the microscope. (When certain areas can't be reached with thoracoscopy, a surgeon may need to make a larger incision in the chest wall, known as a thoracotomy.)

Thoracoscopy can also be used as part of the treatment to remove part of a lung in some early-stage lung cancers.

Immunohistochemistry

For this test, very thin slices of the sample are attached to glass microscope slides. The samples are then treated with special proteins (antibodies) designed to attach only to a specific substance found in certain cancer cells. If the patient's cancer cells contain that substance, the antibody will attach to the cells. Chemicals are then added so that antibodies attached to the cells change color.

Molecular Tests

In some cases, specific gene changes in the cancer cells may be examined.

For example, epidermal growth factor receptor (EGFR) is a protein that sometimes appears in high amounts on the surface of cancer cells and helps them grow. Some newer anti-cancer drugs that target EGFR seem to work best against lung cancers with certain changes in the EGFR gene, which are more common in certain groups, such as non-smokers, women, and Asians, but these drugs don't seem to be as helpful in patients whose cancer cells have changes in the KRAS gene. Many doctors now test for changes in genes such as EGFR and KRAS to determine if these treatments are likely to be helpful.

About 5% of NSCLCs have been found to have a rearrangement in a gene called ALK. This change is most often seen in non-smokers (or light smokers) who have the adenocarcinoma subtype of NSCLC. Doctors may test cancers for changes in the ALK gene to see if a drug (such as crizotinib) that targets this change may be effective.

About 1% to 2% of NSCLCs have a rearrangement in the ROS1 gene, which might make the tumor respond to the targeted drug crizotinib. A similar percentage have a rearrangement in the RET gene. Certain drugs that target cells with RET gene changes might be options for treating these tumors.

Blood Tests

Blood tests are not used to diagnose lung cancer but can help to get a sense of a person's overall health; for example, to see if a person is healthy enough to have surgery.

A complete blood count (CBC) determines whether a subject's blood has normal numbers of various cell types. For example, it can show if one is anemic (have a low number of red blood cells), if one could have trouble with bleeding (due to a low number of blood platelets), or if one is at increased risk for infections (because of a low number of white blood cells). Because chemotherapy can affect blood-forming cells of the bone marrow, this test is repeated regularly.

Blood chemistry tests can help spot abnormalities in for example, the liver or kidneys. For example, if cancer has spread to the liver and bones, it may cause abnormal levels of lactate dehydrogenase (LDH).

Pulmonary Function Tests

Pulmonary function tests (PFTs) are often done after lung cancer is diagnosed to see how well the lungs are working (for example, how much emphysema or chronic bronchitis is present) to provide a surgeon with an idea of whether surgery is a good option, and if so, how much lung can safely be removed. This is especially important if surgery might be an option in treating the cancer, since surgery to remove lung cancer may mean removing part or all of a lung. Some people with poor lung function (like those with lung damage from smoking) do not have enough lung reserve to withstand removing even part of a lung.

Sometimes PFTs are coupled with an arterial blood gas test, in which blood is removed from an artery (most blood tests use blood removed from a vein) to measure the amount of oxygen and carbon dioxide that it contains.

Staging of Lung Cancer

There are two types of stages for lung cancer, a clinical stage and a pathologic stage. The clinical stage is based on the results of the physical exam, biopsies, and imaging tests (CT scan, chest x-ray, PET scan, etc.). The pathologic stage is based on the same factors as the clinical stage, plus what is found as a result of surgery.

Because many patients with lung cancer do not have surgery, the clinical stage is often used when describing the extent of this cancer. When it is available, the pathologic stage is likely to be more accurate than the clinical stage, as it uses the additional information obtained at surgery.

The TNM Staging System

The system used to describe the growth and spread of lung cancer is the American Joint Committee on Cancer (AJCC) TNM staging system. The TNM system is based on 3 key pieces of information:

T indicates the size of the main (primary) tumor and whether it has grown into nearby areas.

N describes the spread of cancer to nearby (regional) lymph nodes. Lymph nodes are small bean-shaped collections of immune system cells to which cancers often spread before going to other parts of the body.

M indicates whether the cancer has spread (metastasized) to other organs of the body. (The most common sites are the brain, bones, adrenal glands, liver, kidneys, and the other lung.)

Numbers or letters appear after T, N, and M to provide more details about each of these factors. The numbers 0 through 4 indicate increasing severity.

T Categories for Lung Cancer

TX: The main (primary) tumor can't be assessed, or cancer cells were seen on sputum cytology or bronchial washing but no tumor can be found.

T0: There is no evidence of a primary tumor.

Tis: The cancer is found only in the top layers of cells lining the air passages. It has not invaded into deeper lung tissues. This is also known as carcinoma in situ.

T1: The tumor is no larger than 3 centimeters (cm)—slightly less than 1¼ inches—across, has not reached the membranes that surround the lungs (visceral pleura), and does not affect the main branches of the bronchi.

If the tumor is 2 cm (about ⅘ of an inch) or less across, it is called T1a. If the tumor is larger than 2 cm but not larger than 3 cm across, it is called T1b.

T2: The tumor has 1 or more of the following features:

It is larger than 3 cm across but not larger than 7 cm.

It involves a main bronchus, but is not closer than 2 cm (about ¾ inch) to the carina (the point where the windpipe splits into the left and right main bronchi).

It has grown into the membranes that surround the lungs (visceral pleura).

The tumor partially clogs the airways, but this has not caused the entire lung to collapse or develop pneumonia.

If the tumor is 5 cm or less across, it is called T2a. If the tumor is larger than 5 cm across (but not larger than 7 cm), it is called T2b.

T3: The tumor has 1 or more of the following features:

It is larger than 7 cm across.

It has grown into the chest wall, the breathing muscle that separates the chest from the abdomen (diaphragm), the membranes surrounding the space between the two lungs (mediastinal pleura), or membranes of the sac surrounding the heart (parietal pericardium).

It invades a main bronchus and is closer than 2 cm (about ¾ inch) to the carina, but it does not involve the carina itself It has grown into the airways enough to cause an entire lung to collapse or to cause pneumonia in the entire lung.

Two or more separate tumor nodules are present in the same lobe of a lung.

T4: The cancer has 1 or more of the following features:

A tumor of any size has grown into the space between the lungs (mediastinum), the heart, the large blood vessels near the heart (such as the aorta), the windpipe (trachea), the tube connecting the throat to the stomach (esophagus), the backbone, or the carina.

Two or more separate tumor nodules are present in different lobes of the same lung.

N Categories for Lung Cancer

NX: Nearby lymph nodes cannot be assessed.

N0: There is no spread to nearby lymph nodes.

N1: The cancer has spread to lymph nodes within the lung and/or around the area where the bronchus enters the lung (hilar lymph nodes). Affected lymph nodes are on the same side as the primary tumor.

N2: The cancer has spread to lymph nodes around the carina (the point where the windpipe splits into the left and right bronchi) or in the space between the lungs (mediastinum). Affected lymph nodes are on the same side as the primary tumor.

N3: The cancer has spread to lymph nodes near the collarbone on either side, and/or spread to hilar or mediastinal lymph nodes on the side opposite the primary tumor.

M Categories for Lung Cancer

M0: No spread to distant organs or areas. This includes the other lung, lymph nodes further away than those mentioned in the N stages above, and other organs or tissues such as the liver, bones, or brain.

M1a: Any of the following:

The cancer has spread to the other lung.

Cancer cells are found in the fluid around the lung (called a malignant pleural effusion).

Cancer cells are found in the fluid around the heart (called a malignant pericardial effusion).

M1b: The cancer has spread to distant lymph nodes or to other organs such as the liver, bones, or brain.

Stage Grouping for Lung Cancer

Once the T, N, and M categories have been assigned, this information is combined to assign an overall stage of 0, I, II, III, or IV. This process is called stage grouping. Some stages are subdivided into A and B. The stages identify cancers that have a similar outlook (prognosis) and thus are treated in a similar way. Patients with lower stage numbers tend to have a better outlook.

Occult (Hidden) Cancer

TX, N0, M0: Cancer cells are seen in a sample of sputum or other lung fluids, but the cancer isn't found with other tests, so its location can't be determined.

Stage 0

T is, N0, M0: The cancer is found only in the top layers of cells lining the air passages. It has not invaded deeper into other lung tissues and has not spread to lymph nodes or distant sites.

Stage IA

T1a/T1b, N0, M0: The cancer is no larger than 3 cm across, has not reached the membranes that surround the lungs, and does not affect the main branches of the bronchi. It has not spread to lymph nodes or distant sites.

Stage IB

T2a, N0, M0: The cancer has 1 or more of the following features:

The main tumor is larger than 3 cm across but not larger than 5 cm.

The tumor has grown into a main bronchus, but is not within 2 cm of the carina (and it is not larger than 5 cm).

The tumor has grown into the visceral pleura (the membranes surrounding the lungs) and is not larger than 5 cm.

The tumor is partially clogging the airways (and is not larger than 5 cm).

The cancer has not spread to lymph nodes or distant sites.

Stage IIA

Three main combinations of categories make up this stage.

T1a/T1b, N1, M0: The cancer is no larger than 3 cm across, has not grown into the membranes that surround the lungs, and does not affect the main branches of the bronchi. It has spread to lymph nodes within the lung and/or around the area where the bronchus enters the lung (hilar lymph nodes). These lymph nodes are on the same side as the cancer. It has not spread to distant sites.

OR

T2a, N1, M0: The cancer has 1 or more of the following features:

The main tumor is larger than 3 cm across but not larger than 5 cm.

The tumor has grown into a main bronchus, but is not within 2 cm of the carina (and it is not larger than 5 cm).

The tumor has grown into the visceral pleura (the membranes surrounding the lungs) and is not larger than 5 cm.

The tumor is partially clogging the airways (and is not larger than 5 cm).

The cancer has also spread to lymph nodes within the lung and/or around the area where the bronchus enters the lung (hilar lymph nodes). These lymph nodes are on the same side as the cancer. It has not spread to distant sites.

OR

T2b, N0, M0: The cancer has 1 or more of the following features:

The main tumor is larger than 5 cm across but not larger than 7 cm.

The tumor has grown into a main bronchus, but is not within 2 cm of the carina (and it is between 5 and 7 cm across).

The tumor has grown into the visceral pleura (the membranes surrounding the lungs) and is between 5 and 7 cm across.

The tumor is partially clogging the airways (and is between 5 and 7 cm across).

The cancer has not spread to lymph nodes or distant sites.

Stage IIB

Two combinations of categories make up this stage.

T2b, N1, M0: The cancer has 1 or more of the following features:

The main tumor is larger than 5 cm across but not larger than 7 cm.

The tumor has grown into a main bronchus, but is not within 2 cm of the carina (and it is between 5 and 7 cm across).

The tumor has grown into the visceral pleura (the membranes surrounding the lungs) and is between 5 and 7 cm across.

The cancer is partially clogging the airways (and is between 5 and 7 cm across).

It has also spread to lymph nodes within the lung and/or around the area where the bronchus enters the lung (hilar lymph nodes). These lymph nodes are on the same side as the cancer. It has not spread to distant sites.

OR

T3, N0, M0: The main tumor has 1 or more of the following features:

It is larger than 7 cm across.

It has grown into the chest wall, the breathing muscle that separates the chest from the abdomen (diaphragm), the membranes surrounding the space between the lungs (mediastinal pleura), or membranes of the sac surrounding the heart (parietal pericardium).

It invades a main bronchus and is closer than 2 cm (about ¾ inch) to the carina, but it does not involve the carina itself.

It has grown into the airways enough to cause an entire lung to collapse or to cause pneumonia in the entire lung.

Two or more separate tumor nodules are present in the same lobe of a lung.

The cancer has not spread to lymph nodes or distant sites.

Stage IIIA

Three main combinations of categories make up this stage.

T1 to T3, N2, M0: The main tumor can be any size. It has not grown into the space between the lungs (mediastinum), the heart, the large blood vessels near the heart (such as the aorta), the windpipe (trachea), the tube connecting the throat to the stomach (esophagus), the backbone, or the carina. It has not spread to different lobes of the same lung.

The cancer has spread to lymph nodes around the carina (the point where the windpipe splits into the left and right bronchi) or in the space between the lungs (mediastinum). These lymph nodes are on the same side as the main lung tumor. The cancer has not spread to distant sites.

OR

T3, N1, M0: The cancer has 1 or more of the following features:

It is larger than 7 cm across.

It has grown into the chest wall, the breathing muscle that separates the chest from the abdomen (diaphragm), the membranes surrounding the space between the lungs (mediastinal pleura), or membranes of the sac surrounding the heart (parietal pericardium).

It invades a main bronchus and is closer than 2 cm to the carina, but it does not involve the carina itself Two or more separate tumor nodules are present in the same lobe of a lung.

It has grown into the airways enough to cause an entire lung to collapse or to cause pneumonia in the entire lung.

It has also spread to lymph nodes within the lung and/or around the area where the bronchus enters the lung (hilar lymph nodes). These lymph nodes are on the same side as the cancer. It has not spread to distant sites.

OR

T4, N0 or N1, M0: The cancer has 1 or more of the following features:

A tumor of any size has grown into the space between the lungs (mediastinum), the heart, the large blood vessels near the heart (such as the aorta), the windpipe (trachea), the tube connecting the throat to the stomach (esophagus), the backbone, or the carina.

Two or more separate tumor nodules are present in different lobes of the same lung.

It may or may not have spread to lymph nodes within the lung and/or around the area where the bronchus enters the lung (hilar lymph nodes). Any affected lymph nodes are on the same side as the cancer. It has not spread to distant sites.

Stage IIIB

Two combinations of categories make up this stage.

Any T, N3, M0: The cancer can be of any size. It may or may not have grown into nearby structures or caused pneumonia or lung collapse. It has spread to lymph nodes near the collarbone on either side, and/or has spread to hilar or mediastinal lymph nodes on the side opposite the primary tumor. The cancer has not spread to distant sites.

OR

T4, N2, M0: The cancer has 1 or more of the following features:

A tumor of any size has grown into the space between the lungs (mediastinum), the heart, the large blood vessels near the heart (such as the aorta), the windpipe (trachea), the tube connecting the throat to the stomach (esophagus), the backbone, or the carina.

Two or more separate tumor nodules are present in different lobes of the same lung.

The cancer has also spread to lymph nodes around the carina (the point where the windpipe splits into the left and right bronchi) or in the space between the lungs (mediastinum). Affected lymph nodes are on the same side as the main lung tumor. It has not spread to distant sites.

Stage IV

Two combinations of categories make up this stage.

Any T, any N, M1a: The cancer can be any size and may or may not have grown into nearby structures or reached nearby lymph nodes. In addition, any of the following is true:

The cancer has spread to the other lung.

Cancer cells are found in the fluid around the lung (called a malignant pleural effusion).

Cancer cells are found in the fluid around the heart (called a malignant pericardial effusion).

OR

Any T, any N, M1b: The cancer can be any size and may or may not have grown into nearby structures or reached nearby lymph nodes. It has spread to distant lymph nodes or to other organs such as the liver, bones, or brain.

Treatment of Lung Cancer

Treatment options for patients with lung cancer include surgery, radiation therapy, local treatments, chemotherapy, and targeted therapies.

Surgery

Surgery to remove the cancer (often along with other treatments) may be an option for early stage lung cancer. Types of lung surgery include, for example, pneumonectomy (an entire lung is removed in this surgery), lobectomy (an entire section (lobe) of a lung is removed in this surgery) and segmentectomy or wedge resection (part of a lobe is removed in this surgery).

Radiation Therapy

Radiation therapy uses high-energy rays (such as x-rays) or particles to kill cancer cells. There are two main types of radiation therapy—external beam radiation therapy and brachytherapy (internal radiation therapy).

External Beam Radiation Therapy

External beam radiation therapy (EBRT) focuses radiation from outside the body on the cancer. This is the type of radiation therapy most often used to treat a primary lung cancer or its spread to other organs.

Treatment is much like getting an x-ray, but the radiation dose is stronger. The procedure itself is painless. Each treatment lasts only a few minutes. Most often, radiation treatments to the lungs are given 5 days a week for 5 to 7 weeks, but this can vary.

Standard (conventional) EBRT is used much less often than in the past. Newer techniques help doctors treat lung cancers more accurately while lowering the radiation exposure to nearby healthy tissues. These techniques may offer better success rates and fewer side effects.

Three-dimensional conformal radiation therapy (3D-CRT): 3D-CRT uses special computers to precisely map the location of the tumor(s). Radiation beams are shaped and aimed at the tumor(s) from several directions, which makes it less likely to damage normal tissues.

Intensity modulated radiation therapy (IMRT): IMRT is an advanced form of 3D therapy. It uses a computer-driven machine that moves around the patient as it delivers radiation. Along with shaping the beams and aiming them at the tumor from several angles, the intensity (strength) of the beams can be adjusted to limit the dose reaching the most sensitive normal tissues. This technique is used most often if tumors are near important structures such as the spinal cord. Many major hospitals and cancer centers now use IMRT.

Stereotactic body radiation therapy (SBRT): SBRT, also known as stereotactic ablative radiotherapy (SABR), is sometimes used to treat very early stage lung cancers when surgery isn't an option due to issues with the patient's health or in patients who do not want surgery. Instead of giving small doses of radiation each day for several weeks, SBRT uses very focused beams of high-dose radiation given in fewer (usually 1 to 5) treatments. Several beams are aimed at the tumor from different angles. To target the radiation precisely, the person is put in a specially designed body frame for each treatment. This reduces the movement of the lung tumor during breathing. Like other forms of external radiation, the treatment itself is painless.

Early results with SBRT for smaller lung tumors have been promising, and it seems to have a low risk of complications. It is also being studied for tumors that have spread to other parts of the body, such as the bones or liver.

Stereotactic radiosurgery (SRS): SRS is a type of stereotactic radiation therapy that is given in only one session. It can sometimes be used instead of or along with surgery for single tumors that have spread to the brain. In one version of this treatment, a machine called a Gamma Knife® focuses about 200 beams of radiation on the tumor from different angles over a few minutes to hours. The head is kept in the same position by placing it in a rigid frame. In another version, a linear accelerator (a machine that creates radiation) that is controlled by a computer moves around the head to deliver radiation to the tumor from many different angles. These treatments can be repeated if needed.

Brachytherapy (Internal Radiation Therapy)

In people with lung cancer, brachytherapy is sometimes used to shrink tumors in the airway to relieve symptoms. It is used less often for lung cancer than for other cancers such as head and neck cancers.

For this type of treatment, a small source of radioactive material (often in the form of small pellets) is placed directly into the cancer or into the airway next to the cancer. This is usually done through a bronchoscope, but it may also be done during surgery. The radiation travels only a short distance from the source, limiting the effects on surrounding healthy tissues. The radiation source is usually removed after a short time. Less often, small radioactive "seeds" are left in place permanently, and the radiation gets weaker over several weeks.

Local Treatments
Radiofrequency Ablation (RFA)

This technique might be an option for some small lung tumors that are near the outer edge of the lungs, especially in those who cannot have or do not want surgery. It uses high-energy radio waves to heat the tumor. A thin, needle-like probe is placed through the skin and moved along until the end is in the tumor. Placement of the probe is guided by CT scans. Once it is in place, an electric current is passed through the probe, which heats the tumor and destroys the cancer cells.

Photodynamic Therapy (PDT)

Photodynamic therapy is sometimes used to treat very early stage lung cancers that are still confined to the outer layers of the lung airways when other treatments aren't appropriate. It can also be used to help open up airways blocked by tumors to help people breathe better.

For this technique, a light-activated drug (porfimer sodium (Photofrin®)) is injected into a vein. This drug is more likely to collect in cancer cells than in normal cells.

After a few days, a bronchoscope is passed down the throat and into the lung. This may be done with either local anesthesia and sedation or with general anesthesia. A special laser light on the end of the bronchoscope is aimed at the tumor, which activates the drug and causes the cells to die. The dead cells are then removed a few days later during a bronchoscopy. This process can be repeated if needed.

Laser Therapy

Lasers can sometimes be used to treat very small lung cancers in the linings of airways. They can also be used to help open up airways blocked by larger tumors. The laser is on the end of a bronchoscope, which is passed down the throat and next to the tumor. The doctor then aims the laser beam at the tumor to burn it away. This treatment can usually be repeated, if needed.

Stent Placement

Lung tumors that have grown into an airway can sometimes cause trouble breathing or other problems. To help keep the airway open (often after other treatments such as PDT or laser therapy), a hard silicone or metal tube called a stent may be placed in the airway using a bronchoscope.

Chemotherapy

The chemo drugs most often used for lung cancer are:
Cisplatin
Carboplatin
Paclitaxel (Taxol®)
Albumin-bound paclitaxel (nab-paclitaxel, Abraxane®)
Docetaxel (Taxotere®)
Gemcitabine (Gemzar®)
Vinorelbine (Navelbine®)
Irinotecan (Camptosar®)
Etoposide (VP-16®)
Vinblastine
Pemetrexed (Alimta®)

Most often, treatment for lung cancer uses a combination of two chemotherapeutic drugs.

If a combination is used, it often includes either cisplatin or carboplatin plus one other drug. Sometimes combinations that do not include these drugs, such as gemcitabine with vinorelbine or paclitaxel, may be used.

For those with advanced lung cancers who meet certain criteria, a targeted therapy drug such as bevacizumab (Avastin®) or cetuximab (Erbitux®) may be added to treatment as well. For advanced cancers, the initial chemotherapeutic combination is often given for 4 to 6 cycles.

If the initial chemotherapeutic treatment for advanced lung cancer is no longer working, a second-line treatment may be recommended. Such treatment may include, for example, a single drug such as docetaxel or pemetrexed.

Targeted Therapies
Drugs that Target Tumor Blood Vessel Growth (Angiogenesis)

For tumors to grow, they must form new blood vessels to keep them nourished. Some targeted drugs block this new blood vessel growth (angiogenesis).

Bevacizumab (Avastin®): Bevacizumab is a monoclonal antibody that targets vascular endothelial growth factor (VEGF). It has been shown to prolong survival of patients with advanced non-small cell lung cancer (NSCLC) when it is added to standard chemotherapy regimens as part of first-line treatment. Bevacizumab is given by infusion into a vein every 2 to 3 weeks.

Drugs that Target EGFR

Epidermal growth factor receptor (EGFR) is a protein found on the surface of cells that normally helps the cells to grow and divide. Some NSCLC cells have too much EGFR, which causes them to grow faster.

Erlotinib (Tarceva®): Erlotinib is a drug that blocks EGFR from signaling the cell to grow. It has been shown to help keep some lung tumors under control, especially in women and in people who have never smoked. It is used alone, mainly for advanced NSCLC, if initial treatment with chemotherapy is no longer working. It can also be used as the first treatment in patients whose cancers have a mutation in the EGFR gene.

Cetuximab (Erbitux®): Cetuximab is a monoclonal antibody that targets EGFR. For patients with advanced NSCLC, some doctors may add it to standard chemotherapy as part of first-line treatment. Cetuximab is given by IV infusion, usually once a week.

Afatinib (Gilotrif™): Like erlotinib, afatinib blocks the signal from EGFR that tells cells to grow. It was recently approved to be used (without chemotherapy) as the first treatment for advanced NSCLCs that have certain mutations in the EGFR gene.

Drugs that Target the ALK Gene

About 5% of NSCLCs have been found to have a rearrangement in a gene called ALK. This change is most often seen in non-smokers (or light smokers) who have the adenocarcinoma subtype of NSCLC. The ALK gene rearrangement produces an abnormal ALK protein that causes the cells to grow and spread.

Crizotinib (Xalkori®), a drug that blocks the abnormal ALK protein, has been shown to shrink tumors in more than half of patients whose lung cancers have the ALK gene change, even in those who have already had chemotherapy. It is now often the first drug used (instead of chemotherapy) in patients with the ALK gene rearrangement.

Despite the availability of these treatment options, median survival for SCLC patients with limited disease (LD) is 16-24 months, while median survival for those with extensive disease (ED) is 7-12 months. Zhang, Y and He, J, J. Thoracic Dis. 5(4): 538-548 (2013). Median survival for NSCLC subjects that undergo videoassisted thoracic surgery (VATS) lobectomy has been reported as 49.0 months in patients with a single station of N2 metastasis. Wang, S, et al, Ann. Thorac. Med. 8(3): 170-175 (2013). Whole-body metastatic extent strongly affects survival outcome, even after adjustment for other significant variables in advanced non-squamous NSCLC. Lee D S, et al., Cancer Res. Treat. 45(2): 95-102 (2013). Thus, additional treatments are needed to treat and prolong survival of patients suffering from NSCLC and SCLC.

Osteosarcoma

Osteosarcoma, the most frequent primary solid malignancy of bone, penetrates and destroys the cortex of the bone and extends into the surrounding soft tissue. Untreated, they run a dismal course with local and often metastatic disease progression. Before the introduction of polychemotherapy, >90% of patients with osteosarcoma died from pulmonary metastases (See, Ritter and Bielack, Annals of Oncology, 2010; Supplement 7: vii320-325).

Osteosarcoma predominantly arises in the metaphysis of long bones such as the distal femur, proximal tibia, and proximal humerus during the second decade of life, and may be characterized as either: (i) primary/localized (i.e., originates in/confined to the bone); (ii) metastatic (i.e., spread from the primary osteosarcoma to an organ or tissue located elsewhere in the body); or (iii) recurrent/relapsing (i.e., return of osteosarcoma after treatment and after a period of time during which osteosarcoma cannot be detected).

The incidence of osteosarcoma in the general population is 2-3/million/year, but is higher in adolescence, with annual incidence peaks at 8-11/million/year at 15-19 years of age. Osteosarcomas account for 15% of all solid extracranial cancers in this age group with males being affected 1.4 times more frequently than females (See, Ritter and Bielack, Annals of Oncology, 2010; Supplement 7: vii320-325).

In children and young adults, osteosarcoma usually develops in areas where the bone is growing quickly, such as near the ends of the long bones. Most tumors develop in the bones around the knee, either in the distal femur or the proximal tibia. However, osteosarcoma can develop in any bone, including the bones of the pelvis, shoulder, and jaw. This is especially true in older adults. The incidence of osteosarcoma is increased in several well-defined hereditary disorders associated with germline alterations of tumor suppressor genes such as hereditary retinoblastoma and the Li-Fraumeni cancer family syndrome.

Bone

Grossly, two types of bone may be distinguished: cancellous, trabecular or spongy bone, and cortical, compact, or dense bone.

Cortical bone, also referred to as compact bone or dense bone, is the tissue of the hard outer layer of bones, so-called due to its minimal gaps and spaces. This tissue gives bones their smooth, white, and solid appearance. Cortical bone consists of Haversian sites (the canals through which blood vessels and connective tissue pass in bone) and osteons (the basic units of structure of cortical bone comprising a Haversian canal and its concentrically arranged lamellae), so that in cortical bone, bone surrounds the blood supply. Cortical bone has a porosity of about 5% to about 30%, and accounts for about 80% of the total bone mass of an adult skeleton.

Cancellous Bone (Trabecular or Spongy Bone)

Cancellous bone tissue, an open, cell-porous network also called trabecular or spongy bone, fills the interior of bone and is composed of a network of rod- and plate-like elements that make the overall structure lighter and allows room for blood vessels and marrow so that the blood supply surrounds bone. Cancellous bone accounts for the remaining 20% of total bone mass but has nearly ten times the surface area of cortical bone. It does not contain Haversian sites and osteons and has a porosity of about 30% to about 90%.

The head of a bone, termed the epiphysis, has a spongy appearance and consists of slender irregular bone trabeculae, or bars, which anastomose to form a lattice work, the interstices of which contain the marrow, while the thin outer shell appears dense. The irregular marrow spaces of the epiphysis become continuous with the central medullary cavity of the bone shaft, termed the diaphysis, whose wall is formed by a thin plate of cortical bone.

Both cancellous and cortical bone have the same types of cells and intercellular substance, but they differ from each other in the arrangement of their components and in the ratio of marrow space to bone substance. In cancellous bone, the marrow spaces are relatively large and irregularly arranged, and the bone substance is in the form of slender anastomosing trabeculae and pointed spicules. In cortical bone, the spaces or channels are narrow and the bone substance is densely packed.

With very few exceptions, the cortical and cancellous forms are both present in every bone, but the amount and distribution of each type vary considerably. The diaphyses of the long bones consist mainly of cortical tissue; only the innermost layer immediately surrounding the medullary cavity is cancellous bone. The tabular bones of the head are composed of two plates of cortical bone enclosing marrow space bridged by irregular bars of cancellous bone. The epiphyses of the long bones and most of the short bones consist of cancellous bone covered by a thin outer shell of cortical bone.

Each bone, except at its articular end, is surrounded by a vascular fibroelastic coat, the periosteum. The so-called endosteum, or inner periosteum of the marrow cavity and marrow spaces, is not a well-demarcated layer; it consists of a variable concentration of medullary reticular connective tissue that contains osteogenic cells that are in immediate contact with the bone tissue.

Components of Bone

Bone is composed of cells and an intercellular matrix of organic and inorganic substances.

The organic fraction consists of collagen, glycosaminoglycans, proteoglycans, and glycoproteins. The protein matrix of bone largely is composed of collagen, a family of fibrous proteins that have the ability to form insoluble and rigid fibers. The main collagen in bone is type I collagen.

The inorganic component of bone, which is responsible for its rigidity and may constitute up to two-thirds of its fat-free dry weight, is composed chiefly of calcium phosphate and calcium carbonate, in the form of calcium hydroxyapatite, with small amounts of magnesium hydroxide, fluoride, and sulfate. The composition varies with age and with a number of dietary factors. The bone minerals form long fine crystals that add strength and rigidity to the collagen fibers; the process by which it is laid down is termed mineralization.

Bone Cells

Four cell types in bone are involved in its formation and maintenance. These are 1) osteoprogenitor cells, 2) osteoblasts, 3) osteocytes, and 4) osteoclasts.

Osteoprogenitor Cells

Osteoprogenitor cells arise from mesenchymal cells, and occur in the inner portion of the periosteum and in the endosteum of mature bone. They are found in regions of the embryonic mesenchymal compartment where bone formation is beginning and in areas near the surfaces of growing bones. Structurally, osteoprogenitor cells differ from the mesenchymal cells from which they have arisen. They are irregularly shaped and elongated cells having pale-staining cytoplasm and pale-staining nuclei. Osteoprogenitor cells, which multiply by mitosis, are identified chiefly by their location and by their association with osteoblasts. Some osteoprogenitor cells differentiate into osteocytes. While osteoblasts and osteocytes are no longer mitotic, it has been shown that a population of osteoprogenitor cells persists throughout life.

Osteoblasts

Osteoblasts, which are located on the surface of osteoid seams (the narrow region on the surface of a bone of newly formed organic matrix not yet mineralized), are derived from osteoprogenitor cells. They are immature, mononucleate, bone-forming cells that synthesize collagen and control mineralization. Osteoblasts can be distinguished from osteoprogenitor cells morphologically; generally they are larger than osteoprogenitor cells, and have a more rounded nucleus, a more prominent nucleolus, and cytoplasm that is much more basophilic. Osteoblasts make a protein mixture known as osteoid, primarily composed of type I collagen, which mineralizes to become bone. Osteoblasts also manufacture hormones, such as prostaglandins, alkaline phosphatase, an enzyme that has a role in the mineralization of bone, and matrix proteins.

Osteocytes

Osteocytes, star-shaped mature bone cells derived from ostoblasts and the most abundant cell found in compact bone, maintain the structure of bone. Osteocytes, like osteoblasts, are not capable of mitotic division. They are actively involved in the routine turnover of bony matrix and reside in small spaces, cavities, gaps or depressions in the bone matrix called lacuna. Osteocytes maintain the bone matrix, regulate calcium homeostasis, and are thought to be part of the cellular feedback mechanism that directs bone to form in places where it is most needed. Bone adapts to applied forces by growing stronger in order to withstand them; osteocytes may detect mechanical deformation and mediate bone-formation by osteoblasts.

Osteoclasts

Osteoclasts, which are derived from a monocyte stem cell lineage and possess phagocytic-like mechanisms similar to macrophages, often are found in depressions in the bone referred to as Howship's lacunae. They are large multinucleated cells specialized in bone resorption. During resorption, osteoclasts seal off an area of bone surface; then, when activated, they pump out hydrogen ions to produce a very acid environment, which dissolves the hydroxyapatite component. The number and activity of osteoclasts increase when calcium resorption is stimulated by injection of parathyroid hormone (PTH), while osteoclastic activity is suppressed by injection of calcitonin, a hormone produced by thyroid parafollicular cells.

Bone Matrix

The bone matrix accounts for about 90% of the total weight of compact bone and is composed of microcrystalline calcium phosphate resembling hydroxyapatite (60%) and fibrillar type I collagen (27%). The remaining 3% consists of minor collagen types and other proteins including osteocalcin, osteonectin, osteopontin, bone sialoprotein, as well as proteoglycans, glycosaminoglycans, and lipids.

Bone matrix is also a major source of biological information that skeletal cells can receive and act upon. For example, extracellular matrix glycoproteins and proteoglycans in bone bind a variety of growth factors and cytokines, and serve as a repository of stored signals that act on osteoblasts and osteoclasts. Examples of growth factors and cytokines found in bone matrix include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

There is an emerging understanding that extracellular matrix molecules themselves can serve regulatory roles, providing both direct biological effects on cells as well as key spatial and contextual information.

The Periosteum and Endosteum

The periosteum is a fibrous connective tissue investment of bone, except at the bone's articular surface. Its adherence to the bone varies by location and age. In young bone, the periosteum is stripped off easily. In adult bone, it is more firmly adherent, especially so at the insertion of tendons and ligaments, where more periosteal fibers penetrate into the bone as the perforating fibers of Sharpey (bundles of collagenous fibers that pass into the outer circumferential lamellae of bone). The periosteum consists of two layers, the outer of which is composed of coarse, fibrous connective tissue containing few cells but numerous blood vessels and nerves. The inner layer, which is less vascular but more cellular, contains many elastic fibers. During growth, an osteogenic layer of primitive connective tissue forms the inner layer of the periosteum. In the adult, this is represented only by a row of scattered, flattened cells closely applied to the bone. The periosteum serves as a supporting bed for the blood vessels and nerves going to the bone and for the anchorage of tendons and ligaments. The osteogenic layer, which is considered a part of the periosteum, is known to furnish osteoblasts for growth and repair, and acts as an important limiting layer controlling and restricting the extend of bone formation. Because both the periosteum and its contained bone are regions of the connective tissue compartment, they are not separated from each other or from other connective tissues by basal laminar material or basement membranes. Perosteal stem cells have been shown to be important in bone regeneration and repair. (Zhang et al., 2005, J. Musculoskelet. Neuronal. Interact. 5(4): 360-362).

The endosteum lines the surface of cavities within a bone (marrow cavity and central canals) and also the surface of trabeculae in the marrow cavity. In growing bone, it consists of a delicate striatum of myelogenous reticular connective tissue, beneath which is a layer of osteoblasts. In the adult, the osteogenic cells become flattened and are indistinguishable as a separate layer. They are capable of transforming into osteogenic cells when there is a stimulus to bone formation, as after a fracture.

Marrow

The marrow is a soft connective tissue that occupies the medullary cavity of the long bones, the larger central canals, and all of the spaces between the trabeculae of spongy bone. It consists of a delicate reticular connective tissue, in the meshes of which lie various kinds of cells. Two varieties of marrow are recognized: red and yellow. Red marrow is the only type found in fetal and young bones, but in the adult it is restricted to the vertebrae, sternum, ribs, cranial bones, and epiphyses of long bones. It is the chief site for the genesis of blood cells in the adult body. Yellow marrow consists primarily of fat cells that gradually have replaced the other marrow elements. Under certain conditions, the yellow marrow of old or emaciated persons loses most of its fat and assumes a reddish color and gelatinous consistency, known as gelatinous marrow. With adequate stimulus, yellow marrow may resume the character of red marrow and play an active part in the process of blood development.

Osteogenesis or Ossification

Osteogenesis or ossification is a process by which the bones are formed. There are three distinct lineages that generate the skeleton. The somites generate the axial skeleton, the lateral plate mesoderm generates the limb skeleton, and the cranial neural crest gives rise to the branchial arch, craniofacial bones, and cartilage. There are two major modes of bone formation, or osteogenesis, and both involve the transformation of a preexisting mesenchymal tissue into bone tissue. The direct conversion of mesenchymal tissue into bone is called intramembranous ossification. This process occurs primarily in the bones of the skull. In other cases, mesenchymal cells differentiate into cartilage, which is later replaced by bone. The process by which a cartilage intermediate is formed and replaced by bone cells is called endochondral ossification.

Intramembranous Ossification

Intramembraneous ossification is the characteristic way in which the flat bones of the scapula, the skull and the turtle shell are formed. In intramembraneous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembraneous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranous ossification involves bone morphogenetic proteins (BMPs) and the activation of a transcription factor called CBFA1. Bone morphogenetic proteins, for example, BMP2, BMP4, and BMP7, from the head epidermis are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

Endochondral Ossification (Intracartilaginous Ossification)

Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Pax1 and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

Bone Remodeling

Bone constantly is broken down by osteoclasts and re-formed by osteoblasts in the adult. It has been reported that as much as 18% of bone is recycled each year through the process of renewal, known as bone remodeling, which maintains bone's rigidity. The balance in this dynamic process shifts as people grow older: in youth, it favors the formation of bone, but in old age, it favors resorption.

As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

Bone Regeneration and Fracture Repair

A fracture, like any traumatic injury, causes hemorrhage and tissue destruction. The first reparative changes thus are characteristic of those occurring in any injury of soft tissue. Proliferating fibroblasts and capillary sprouts grow into the blood clot and injured area, thus forming granulation tissue. The area also is invaded by poly morphonuclear leukocytes and later by macrophages that phagocytize the tissue debris. The granulation tissue gradually becomes denser, and in parts of it, cartilage is formed. This newly formed connective tissue and cartilage is designated as a callus. It serves temporarily in stabilizing and binding together the fracture bone. As this process is taking place, the dormant osteogenic cells of the periosteum enlarge and become active osteoblasts. On the outside of the fractured bone, at first at some distance from the fracture, osseous tissue is deposited. This formation of new bone continues toward the fractured ends of the bone and finally forms a sheath-like layer of bone over the fibrocartilaginous callus. As the amount of bone increases, osteogenic buds invade the fibrous and cartilaginous callus and replace it with a bony one. The cartilage undergoes calcification and absorption in the replacement of the fibrocartilaginous callus and intramembraneous bone formation also takes place. The newly formed bone is at first a spongy and not a compact type, and the callus becomes reduced in diameter. At the time when this subperiosteal bone formation is taking place, bone also forms in the marrow cavity. The medullary bone growing centripetally from each side of the fracture unites, thus aiding the bony union.

The process of repair is, in general, an orderly process, but it varies greatly with the displacement of the fractured ends of the bone and the degree of trauma inflicted. Uneven or protruding surfaces gradually are removed, and the healed bone, especially, in young individuals, assumes its original contour.

Osteogenesis and Angiogenesis

Skeletal development and fracture repair includes the coordination of multiple events such as migration, differentiation, and activation of multiple cell types and tissues. The development of a microvasculature and microcirculation is important for the homeostasis and regeneration of living bone, without which the tissue would degenerate and die. Recent developments using in vitro and in vivo models of osteogenesis and fracture repair have provided a better understanding of the recruitment nature of the vasculature in skeletal development and repair.

The vasculature transports oxygen, nutrients, soluble factors and numerous cell types to all tissues in the body. The growth and development of a mature vascular structure is one of the earliest events in organogenesis. In mammalian embryonic development, the nascent vascular networks develop by aggregation of de novo forming angioblasts into a primitive vascular plexus (vasculogenesis). This undergoes a complex remodeling process in which sprouting, bridging and growth from existing vessels (angiogenesis) leads to the onset of a functional circulatory system.

The factors and events that lead to the normal development of the embryonic vasculature are recapitulated during situations of neoangiogenesis in the adult. There are a number of factors involved in neoangiogenesis; these include, but are not limited to, Vascular Endothelial Growth Factor (VEGF), basic Fibroblast Growth Factor (bFGF), various members of the Transforming Growth factor beta (TGFβ) family and Hypoxia-Inducible Transcription Factor (HIF). Other factors that have angiogenic properties include the Angiopoietins, (Ang-1); Hepatocyte Growth Factor (HGF); Platelet-Derived Growth Factor (PDGF); Insulin-like Growth Factor family (IGF-1, IGF-2) and the Neurotrophins (NGF).

The VEGFs and their corresponding receptors are key regulators in a cascade of molecular and cellular events that ultimately lead to the development of the vascular system, either by vasculogenesis, angiogenesis or in the formation of the lymphatic vascular system. Although VEGF is a critical regulator in physiological angiogenesis, it also plays a significant role in skeletal growth and repair.

In the mature established vasculature, the endothelium plays an important role in the maintenance of homeostasis of the surrounding tissue by providing the communicative network to neighboring tissues to respond to requirements as needed. Furthermore, the vasculature provides growth factors, hormones, cytokines, chemokines and metabolites, and the like, needed by the surrounding tissue and acts as a barrier to limit the movement of molecules and cells. Signals and attractant factors expressed on the bone endothelium help recruit circulating cells, particularly hematopoietic cells, to the bone marrow and coordinate with metastatic cells to target them to skeletal regions. Thus, any alteration in the vascular supply to bone tissue can lead to skeletal pathologies, such as osteonecrosis (bone death caused by reduced blood flow to bones), osteomyelitis (infection of the bone or bone marrow by microorganism), and osteoporosis (loss of bone density). A number of factors have been found to have a prominent effect on the pathology of the vasculature and skeleton, including Osteoprotegerin (OPG), which inhibits Receptor Activator of NF-κB Ligand (RANKL)-induced osteoclastogenic bone resorption.

Both intramembraneous and endochondral bone ossification occur in close proximity to vascular ingrowth. In endochondral ossification, the coupling of chondrogenesis and osteogenesis to determine the rate of bone ossification is dependent on the level of vascularization of the growth plate. For example, vascular endothelial growth (VEGF) factor isoforms are essential in coordinating metaphyseal and epiphyseal vascularization, cartilage formation, and ossification during endochondral bone development. HIF-1 stimulates transcription of the VEGF gene (and of other genes whose products are needed when oxygen is in short supply). The VEGF protein is secreted, diffuses through the tissue, and acts on nearby endothelial cells.

The response of the endothelial cells includes at least four components. First, the cells produce proteases to digest their way through the basal lamina of the parent capillary or venule. Second, the endothelial cells migrate toward the source of the signal. Third, the cells proliferate. Fourth, the cells form tubes and differentiate. VEGF acts on endothelial cells selectively to stimulate this entire set of effects. Other growth factors, including some members of the fibroblast growth factor family, also can stimulate angiogenesis, but they influence other cell types besides endothelial cells. As the new vessels form, bringing blood to the tissue, the oxygen concentration rises, HIF-1 activity declines, VEGF production is shut off, and angiogenesis ceases.

The vascularization of cartilage regions in long bones occurs at different stages of development. In early embryonic development, blood vessels that originate from the perichondrium invaginate into the cartilage structures. During elevated postnatal growth, capillaries invade the growth plate of long bones. In adulthood, angiogenesis periodically can be switched on during bone remodeling in response to bone trauma or pathophysiological conditions such as rheumatoid arthritis (RA) and osteoarthritis (OA).

Bone has the unique capacity to regenerate without the development of a fibrous scar, which is symptomatic of soft tissue healing of wounds. This is achieved through the complex interdependent stages of the healing process, which mimic the tightly regulated development of the skeleton. Following trauma with damage to the musculoskeletal system, disruption of the vasculature leads to acute necrosis and hypoxia of the surrounding tissue. This disruption of the circulation leads to the activation of thrombotic factors in a coagulation cascade leading to the formation of a hematoma. The inflammatory response and tissue breakdown activate factors such as cytokines and growth factors that recruit osteoprogenitor and mesenchymal cells to the fracture site. The stimulation of the endosteal circulation in the fractured bone allows mesenchymal cells associated with growing capillaries to invade the wound region from the endosteum and bone marrow. At the edge of a bone fracture, the transiently formed granulation tissue is replaced by fibrocartilage. Concomitantly, the periosteum directly undergoes intramembranous bone formation leading to the formation of an external callus; while internally, the tissue is being mineralized to form woven bone. After stabilization of the bone tissue and vasculature in the bone fracture, the cell mediated remodeling cascade is activated where osteoclastic removal of necrotic bone is followed by the replacement of the large fracture callus by lamellar bone, the callus size is reduced and the normal vascular supply is restored.

A plurality of mediators associated with fetal and postnatal bone development plays a prominent role in the cascade response in bone fracture repair. These include but are not limited to BMP-2 and 4, VEGF, bFGF, TGF-β, and PDGF. VEGF expression is detected on chondroblasts, chondrocytes, osteoprogenitor cells and osteoblasts in the fracture callus where it is highly expressed in angioblasts, osteoprogenitor and osteoblast cells during the first seven days of healing but decreases after eleven days. Additionally, osteoclasts release heparinase that induces the release of the active form of VEGF from heparin, activating not only angiogenesis but also osteoclast recruitment, differentiation and activity leading to the remodeling of the fracture callus during endochondral ossification. Fractures in some cases fail to repair or unite resulting in fibrous filled pseudarthrosis. A number of contributing factors can lead to non-union or delayed union of bone fractures, such as, but not limited to, anti-inflammatory drugs, steroids, Vitamin C, Vitamin D and calcium deficiencies, tobacco smoking, diabetes, and other physiological disorders.

The absence of a functional vascular network is also an important factor in the lack of bone healing in non-union fractures. Studies have reported that angiogenic factors released from biomimetic scaffolds can enhance bone regeneration and that combination strategies that release both angiogenic and osteogenic factors can enhance the regenerative capacity of bone.

The critical sequential timing of osteoclast differentiation and activation, angiogenesis, recruitment of osteoprogenitor cells and the release of growth factors such as BMP-2 in osteogenesis and fracture repair may be enhanced by the synchronized endogenous production of angiogenic and osteogenic mediators. Studies in rat femoral drill-hole injury have shown differential expression of VEGF splicing isoforms along with its receptors, indicating an important role in the bone healing process. Other studies have demonstrated that angiogenesis occurs predominantly before the onset of osteogenesis in bone lengthening in an osteodistraction model.

Another angiogenic inducing growth factor, FGF-2, can accelerate fracture repair when added exogenously to the early healing stage of a bone. Although the mechanism has not been fully elucidated, it has the ability to stimulate angiogenesis and the proliferation and differentiation of osteoblasts to possibly aid the repair of bone fractures.

Osteosarcoma

Osteosarcoma is defined pathologically by its production of osteoid (newly formed organic bone matrix) prior to calcification. Considerable variability exists in the predominant matrix produced, described as the histologic subtype, but the presence of even a small area of osteoid in association with a malignant spindle cell is used to make the diagnosis. It remains unknown whether the clinical features of osteosarcoma are defined by the cell of origin, the genetic events leading to transformation, the timing of those events, or factors related to differentiation into an osteoblastic phenotype. R. Gorlick, Cancer Treatment & Res. 152: 467-478 (2010). In a mouse model, osteosarcoma was shown to develop from mesenchymal stem cells through genomic loss of the cdkn2 region. Mohseny, A B et al., J. Pathol. 219(3): 294-305 (2009).

Subtypes of Osteosarcoma

High-Grade Osteosarcomas

High-grade osteosarcomas are the fastest growing types of osteosarcoma and occur most often in children and teens. The neoplastic cells in high grade conventional osteosarcoma have marked nuclear pleiomorphism, conspicuous chromatin abnormalities, prominent nucleoli and many mitotic figures, some of which are atypical. High-grade osteosarcomas include osteoblastic, chondroblastic, fibroblastic, mixed, small cell, telangiectatic, high-grade surface (juxtacortical high grade), pagetoid (a tumor that develops in someone with Paget disease of the bone), extra-skeletal (a tumor that starts in a part of the body other than a bone) and post-radiation (a tumor that starts in a bone that had once received radiation therapy). In the fibrosarcomatous pattern of osteosarcoma, the stroma is composed of spindle cells.

Intermediate-Grade Osteosarcomas

Intermediate-grade osteosarcomas are uncommon tumors that fall between high-grade and low-grade osteosarcomas but are treated as if they are low-grade osteosarcomas. An example of an intermediate-grade osteosarcoma is periosteal (juxtacortical intermediate grade).

Low-Grade Osteosarcomas

Low-grade osteosarcomas are the slowest growing osteosarcomas. These tumors appear as normal bone and have few dividing cells when seen under a microscope. Two types of these tumors are parosteal (juxtacortical low grade) and intramedullary/intraosseous well differentiated (low-grade central).

Staging of Osteosarcoma

The treatment and prognosis for osteosarcoma depend, to a large extent, on the stage of the cancer when it is first diagnosed.

Primary/Localized Osteosarcoma

Primary osteosarcoma is seen only in the bone in which it started while localized osteosarcoma is found in the tissues next to the bone, such as muscle, tendon, or fat. Approximately 80% of osteosarcomas are thought to be localized when they are first detected. In fact, most patients have micrometastases at the time of diagnosis, emphasizing the importance of chemotherapy as a treatment for most osteosarcomas.

Doctors further divide localized osteosarcomas into two groups: (i) resectable cancers; and (ii) non-resectable/unresectable cancers. Resectable cancers are those in which all of the visible tumor can be removed by surgery. Non-resectable/unresectable cancers are those that cannot be completely removed by surgery.

Metastatic Osteosarcoma

A metastatic osteosarcoma has spread from the primary osteosarcoma to an organ or tissue located elsewhere in the body. Osteosarcoma most often metastasizes to the lungs, but can also spread to other bones, the brain, or other organs. About 20% of osteosarcoma patients have metastatic spread at the time of diagnosis. Patients with metastatic osteosarcoma are harder to treat, but some can be cured if the metastases can be removed by surgery. The cure rate for these patients improves if chemotherapy is combined with surgery.

Grading of Osteosarcoma

There are several grading systems for osteosarcoma. The Musculoskeletal Tumor Society (MTS) staging system for osteosarcoma is based on tumor grade (I=low-grade; II=high-grade), tumor extension (A=intra-compartmental; B=extra-compartmental), and presence of macroscopic distant metastases (III). For example, in the MTS staging system, localized high-grade osteosarcoma is classified as stage IIA or IIB, while metastatic disease, regardless of the extent of the primary lesion, is classified as stage III disease. Another grading system, The American Joint Committee on Cancer (AJCC) staging system is similar to the MTS staging system with a few notable distinctions. The AJCC staging system classifies stage III as any tumor with skip metastases. Skip metastases are tumor nodules growing outside the reactive rim but within the same bone or across a neighboring joint and represent regional intraosseous or transarticular metastases, respectively. In addition, AJCC stages I and II are subdivided into categories A and B based on tumor size being greater or less than 8 cm in any dimension, respectively, rather than tumor extension. This system also uses an extra stage 1V, which is divided into IVA or M1 (describing pulmonary metastases), and IVB or M1b (describing other metastases). The European and American Osteosarcoma Study Group uses the Enneking system to stage bone sarcomas. This system is based on the grade of the tumor (G), the local extent of the primary tumor (T), and metastasis of the tumor to regional lymph nodes or other organs (M). Tumors are classified as either low grade (G1) or high grade (G2), and the extent of the primary tumor is classified as either localized intra-compartmental (T1) or extended extra-compartmental (T2). Tumors that have not spread to the lymph nodes or other organs are classified as M0, while those that have spread are M1. In addition to these clinical grading systems, Meister et al. characterized osteosarcomas as ranging from + to +++ by semi-quantitative evaluation of histological features based on cellular atypism and mitotic activity (See, Dai et al. Med Sci Moni, 2011; 17(8): RA177-190).

Treatment of Osteosarcoma

Before the 1970's, when the treatment for osteosarcoma was mainly limb amputation, the 5-year survival rate of patients was 10-20% (See, Ritter and Bielack, Annals of Oncology, 2010; Supplement 7: vii320-325). The combination of surgery and modern multiagent, dose-intensive chemotherapy increased the 5-year survival rates of patients to about 60-70%. Current protocols for osteosarcoma typically include neoadjuvant (preoperative) therapy, followed by adjuvant (postoperative) therapy, if required. The most commonly administered chemotherapy drugs include cisplatin, doxorubicin, ifosfamide, and high-dose methotrexate with leucovnorin calcium rescue. The therapeutic potential of bisphosphonates such as zoledronic acid, minodronate, risedronate, and alendronate has gained wide recognition in recent years due to their inhibitory effect on the growth of human osteosarcoma cells (See, Dai et al. Med Sci Moni, 2011; 17(8): RA177-190).

Surgery

Surgery remains an indispensable part of osteosarcoma treatment. The goal of surgery is to remove the entire tumor while retaining as much function as possible. Wide surgical margins, as defined by Enneking's criteria for surgical procedures, implying complete removal of the tumor surrounded by normal (i.e., tumor-free) tissue must be attempted (Enneking, W. F. et al., Clin. Orthop. Relat. Res. 1980, 153, 106-120; Bielack, S. et al., Annals of Oncology, 20 (Supplement 4):iv137-iv 139 (2009); Ando, K. et al., Cancers 2013, 5, 591-616).

Tumors in the arms or legs might be treated with either limb-salvage (limb-sparing) surgery or amputation. Limb-salvage surgery removes the cancer without amputation, while amputation removes the cancer and all or part of an arm or leg.

If the osteosarcoma has spread (i.e., metastasized) to other parts of the body, these tumors will be removed surgically, if possible.

Chemotherapy for Osteosarcoma

Systemic chemotherapy is the most common treatment for patients with osteosarcoma since the introduction of chemotherapeutics in the 1970s (Allison, D. C. et al., Sarcoma 2012, 2012, ID 704872; Ando, K. et al., Cancers 2013, 5, 591-616). Most osteosarcomas are treated with systemic chemotherapy given before surgery (neoadjuvant chemotherapy) for about 10 weeks and again after surgery (adjuvant chemotherapy) for up to a year. The current standard protocol consists of either cisplatin or cisplatin in combination with doxorubicin, methotrexate with leukovorin-rescue, with or without ifosfamide (Bielack, S. et al., Annals of Oncology, 20 (Supplement 4):iv137-iv 139 (2009)). Other drugs used to treat osteosarcoma include carboplatin, etoposide, cyclophosphamide, epirubicin, gemcitabine, and topotecan. These regimens are usually employed over a 6-12 month period and provide greater than 60% overall survival for patients with primary/localized osteosarcoma (Bielack, S. et al., Annals of Oncology, 20 (Supplement 4):iv137-iv 139 (2009); Chou, A. J. and Gorlick, R., Expert Rev. Anticancer Ther. 2006, 6, 1075-1085). However, current chemotherapy is associated with acute and long-term toxicities. For example, the potential for hearing loss, neuropathy, kidney damage, nausea, vomiting and hypomagnesemia resulting from cisplatin administration, anthracycline-induced cardiomyopathy associated with doxorubicin administration, leukoencephalopathy, liver damage and kidney damage caused by methotrexate, and sterility in post-pubertal males associated with ifosfamide administration (Meyers, P. A. and Gorlick, R., Pediatr. Clin. North Am., 1997; 44:973-989; Baum, E. S. et al., Cancer Treat. Rep. 1981; 65:815-822; Brock, P. R. et al., Med. Pediatr. Oncol., 1991; 19:295-300; Hayes F. A. et al., Cancer Treat. Rep. 1979; 63:547-548; Von Hoff D. D. et al., Ann. Intern. Med., 1979; 91:710-717; Meistrich, M. L. et al., Cancer, 1989; 63:2115-2123).

Immunomodulation, by alpha-interferon for example, may be another form of osteosarcoma therapy. Indeed, the addition of the immunomodulator liposomal muramyl tripeptide phosphatidyl ethanolamine (MTP) to postoperative chemotherapy was reported to correlate with a statistically significant advantage in overall survival. (See, Ritter and Bielack, Annals of Oncology, 2010; Supplement 7: vii320-325.)

Radiation Therapy for Osteosarcoma

External beam radiation therapy is the type of radiation therapy most often used to treat osteosarcoma. Newer radiation techniques, such as intensity modulated radiation therapy (IMRT) and conformal proton beam therapy, may allow doctors to aim treatment at the tumor more precisely while reducing the amount of radiation to nearby healthy tissues.

Radioactive Drugs (Radiopharmaceuticals)

Bone-seeking radioactive drugs, such as samarium-153, are also sometimes used to treat people with advanced osteosarcoma. These drugs are injected into a vein and collect in bones. Once there, these drugs kill cancer cells and relieve the pain caused by bone metastases.

Stem Cell Therapy

Numerous studies have been conducted to investigate the effect of combining autologous stem cells with high doses of chemotherapy in the treatment of relapsed osteosarcoma. However, these studies have failed to demonstrate an improvement in survival rate (See, Dai et al. Med Sci Moni, 2011; 17(8): RA177-190).

Treatment Based on the Extent of the Osteosarcoma

Treatment for osteosarcoma depends on several factors, including the extent, location, and grade of the cancer, and on a person's overall health.

Localized, Resectable Osteosarcoma

Treatment for localized/resectable osteosarcoma consists of a combination of surgery and chemotherapy (Bielack, S. et al., Annals of Oncology, 20 (Supplement 4):iv137-iv 139 (2009)). Most osteosarcomas are high grade, meaning they may grow and spread quickly if not treated. The usual sequence of treatment for these cancers includes biopsy (to establish the diagnosis), chemotherapy (usually for about 10 weeks), surgery, and additional chemotherapy (for up to a year). This multimodal treatment increases disease-free survival probabilities to greater than 60% (Bielack, S. et al., Annals of Oncology, 20 (Supplement 4):iv137-iv 139 (2009)). In contrast, the disease-free survival probabilities for high grade osteosarcoma patients treated with either surgery alone or chemotherapy alone is 10-20% (Coventry, M. B. et al., J. Bone Joint Surg. Am. 1957, 39, 741-757; Bielack, S. et al., Annals of Oncology, 20 (Supplement 4):iv137-iv 139 (2009); Jaffe, N. et al., Cancer 2002, 95, 2202-2210).

A small number of osteosarcomas are low grade, meaning they are likely to grow slowly. Patients with low-grade, resectable osteosarcomas can often be cured with surgery alone (i.e., without chemotherapy).

Localized, Non-Resectable Osteosarcoma

Localized, non-resectable osteosarcomas have not spread to other parts of the body, but they cannot be completely removed by surgery. For example, they may be too large or too close to vital structures in the body to be resected completely. Chemotherapy is usually the first treatment for these cancers. If the tumor shrinks enough to become resectable after chemotherapy, it will be removed surgically. Additionally, chemotherapy will likely be administered for up to a year after surgery.

If the tumor remains unresectable after chemotherapy, radiation therapy is often used to keep the tumor in check and to relieve symptoms. This may be followed by more chemotherapy.

Metastatic Osteosarcoma

The most common site for metastases of osteosarcoma is the lung, but metastases may occur in bone and other tissues. Patients with metastatic osteosarcoma at the time of diagnosis have a poor prognosis. The overall survival of patients with metastatic osteosarcoma ranges from 10-50%, depending on the location and the number of metastatic foci (Meyers, P. A. et al., J. Clin. Oncol. 1993, 11, 449-453; Ferguson, W. S. et al., J. Pediatr. Hematol. Oncol. 2001, 23, 340-348; Harris, M. B. et al., J. Clin. Oncol. 1998, 16, 3641-3648; Goorin, A. M. et al., J. Clin. Oncol. 2002, 20, 426-433). Despite the poor prognosis, treatment for metastatic osteosarcoma is similar or even identical to that of primary/localized disease with the mandatory addition of surgical removal to all known metastatic foci, usually by exploratory thoracotomy including palpation of the whole lung (Bielack, S. et al., Annals of Oncology, 20 (Supplement 4):iv137-iv 139 (2009); Ritter and Bielack, Annals of Oncology, 2010; Supplement 7: vii320-325).

In addition to chemotherapy, lung metastasectomy (i.e., surgery) has been shown to increase or prolong survival in patients with metastatic disease (Bacci, G. et al., Cancer 1997, 79, 245-254; Briccoli, A. et al., Cancer 2005, 104, 1721-1725; Marcove, R. C. et al., J. Bone Joint Surg. Am. 1973, 55, 1516-1520). The 5-year survival of patients with complete lung metastasectomy is 12-23%, whereas the 5-year survival of patients without aggressive surgical resection is 2.6% (Harting, M. T. et al., Semin. Pediatr. Surg. 2006, 15, 25-29; Ward, W. G. et al., J. Clin. Oncol. 1994, 12, 1849-1858). As with the treatment of primary/localized osteosarcoma, acute and long-term toxicities exist (Meyers, P. A. and Gorlick, R., Pediatr. Clin. North Am., 1997; 44:973-989; Baum, E. S. et al., Cancer Treat. Rep. 1981; 65:815-822; Brock, P. R. et al., Med. Pediatr. Oncol., 1991; 19:295-300; Hayes F. A. et al., Cancer Treat. Rep. 1979; 63:547-548; Von Hoff D. D. et al., Ann. Intern. Med., 1979; 91:710-717; Meistrich, M. L. et al., Cancer, 1989; 63:2115-2123).

Recurrent/Relapse Osteosarcoma

Recurrence of osteosarcoma can occur locally, but is most common in the lung (Ando, K. et al., Cancers 2013, 5, 591-616; Merimsky, O. et al., IMAJ, 2004; 6:34-38). Treatment for recurrent osteosarcoma is primarily surgical (Bielack, S. et al, Annals of Oncology, 20 (Supplement 4):iv137-iv 139 (2009)). The ability to achieve complete resection of recurrent disease is critical as recurrent disease is almost universally fatal (Bielack, S. et al., Annals of Oncology, 20 (Supplement 4):iv137-iv 139 (2009); Merimsky, O. et al., IMAJ, 2004; 6:34-38).

The role of second-line chemotherapy for recurrent osteosarcoma is much less well defined. Presently, there is no standard chemotherapy regimen for osteosarcoma that relapses following multi-modal treatment with surgery and systemic chemotherapy. The choice of chemotherapy may take into account the prior free interval and disease resectability and often includes cisplatin or cisplatin in combination with ifosfamide or etoposide (Bielack, S. et al., Annals of Oncology, 20 (Supplement 4):iv137-iv 139 (2009)). Prognosis for these patients is poor, with long-term post-relapse survival rates of less than 20% (Ferrari, S. et al., J. Clin. Oncol., 2003; 21:710-715; Kempf-Bialek, B. et al., J. Clin. Oncol., 2005; 23:559-568).

Bacci et al. studied treatment and outcome of patients having recurrent osteosarcoma. It was observed that the first relapses were isolated lung metastases in 80% of the patients, isolated distant bone metastases in 8.6% of the patients, and the remaining 7.6% of the patients had isolated metastases in other sites (kidney, heart), more-than-one-site metastases, and isolated local recurrence associated with lung metastases (Bacci et al., Acta Oncologica, 2005; 44: 748-755). Bacci et al. further noted that the mean interval from the start of treatment and the first relapse was longer for patients who relapsed with isolated metastases (29.4 months) than for patients who relapsed with isolated local recurrence (24 months) (Bacci et al., Acta Oncologica, 2005; 44: 748-755). In patients with isolated lung metastases, the rate of remission was significantly correlated with the number of metastatic nodules. For example, the rate of remission for patients with only one or two nodules was 89.2% while the rate of remission for patients with more than two nodules was 46.9% (Bacci et al., Acta Oncologica, 2005; 44: 748-755). For patients treated by surgery alone or surgery combine with second-line chemotherapy, the rate of remission was 95.3% and 81.4%, respectively (Bacci et al., Acta Oncologica, 2005; 44: 748-755).

Bacci et al. also studied second, third, fourth and fifth relapses of lung metastases. The second relapse of isolated lung metastases was in 66.6% of the patients, while isolated metastases in other bones occurred in 15.8% of the patients. Metastases in more than one site occurred in 8.3% of the patients, and isolated local recurrence occurred in 5% of the patients. When patients experienced third, fourth and fifth relapses, the most common site of relapse was the lung (Bacci et al., Acta Oncologica, 2005; 44: 748-755).

Bielack et al. conducted a similar study regarding second and subsequent recurrences of osteosarcoma (Bielack et al., Journal of Clinical Oncology 27:557-565). Postrecurrence survival was observed, and the median survival time was 1.02 years after the second recurrence; 1.02 years after the third recurrence; 0.98 years after the fourth recurrence; and 0.94 years after the fifth recurrence. Intervals between the current and the previous recurrence greater than median generally correlated with better outcomes, as did a history of having had a longer first recurrence-free interval. Patients with solitary lesions had a better outcome than those with multiple lesions, and patients with lung metastases had a better outcome if the metastases were unilateral (Bielack et al., Journal of Clinical Oncology 27:557-565). Overall, the 5-year survival estimate for patients who again achieved surgical remissions after subsequent rerecurrences was only about 25% (Bielack et al., Journal of Clinical Oncology 27:557-565).

Despite the poor prognosis, there is no satisfactory alternative to metastasectomy and systemic chemotherapy for the treatment of recurrent osteosarcoma. Thus, the need exists to develop alternative treatments to maintain quality of life and prolong survival of these patients.

Cisplatin

Cisplatin (cis-diaminedichloroplatinum (II)) is one of the oldest, effective agents used in the systemic treatment of cancer. Since first used in clinical trials for cancer treatment in 1971, cisplatin has been used not only to treat osteosarcoma, but also, for example, bladder cancer, cervical cancer, malignant mesothelioma, non-small cell lung cancer, ovarian cancer, squamous cell carcinoma of the head and neck and testicular cancer (http: cancer.gov/cancertopics/drug-info).

Cisplatin is thought to exert its anticancer effects by interacting with DNA and subsequently inducing programmed cell death (i.e., apoptosis). Cisplatin enters a tumor cell either by diffusing through the cell membrane or by active transport via Cu-transporting proteins (Gately, D. P. and Howell, S., Br. J. Cancer, 1993, 67:1171-1176; Ishida, S. et al., PNAS, 2002; 99:14298-14302). Once inside the tumor cell, cisplatin reacts with one of the DNA bases, usually guanine, to form a monofunctional DNA adduct (Alderden, R. A. et al., JCE, 2006; 83(5):728-734). Subsequent bifunctional adducts (e.g., guanine-guanine and/or adenine-guanine) may occur, causing significant distortion of the DNA that can be recognized by one or more DNA binding proteins (Jamieson, E. R. and Lippard, S. J., Chem. Rev. 1999; 99:2467-2498; Hambley, T. W., Dalton Trans., 2001; 2711-2718; Cohen, G. L. et al., J. Am. Chem. Soc., 1980; 102:2487-2488). The DNA binding proteins either initiate DAN damage repair or signal for apoptosis (Jamieson, E. R. and Lippard, S. J., Chem. Rev. 1999; 99:2467-2498; Hambley, T. W., Dalton Trans., 2001; 2711-2718; Kelland, L. R., Drugs, 2000; 59 Suppl., 1-8; Fuertes, M. A. et al., Curr. Med. Chem. Anti-Cancer Agents, 2002; 2:539-551).

Following administration into the bloodstream, cisplatin is vulnerable to attack by proteins found in blood plasma, particularly proteins that contain thiol groups (Alderden, R. A. et al., JCE, 2006; 83(5):728-734). Studies have shown that one day after cisplatin administration, 65-98% of the platinum in blood plasma is protein bound (Ivanov, A. I. et al., J. Biol. Chem. 1998; 273:14721-14730; DeConti, R. C. et al., Cancer Res. 1973; 33:1310-1315). This protein binding has been blamed for deactivation of the drug as well as some of the severe side effects associated with cisplatin treatment (Ivanov, A. I. et al., J. Biol. Chem. 1998; 273: 14721-14730; Barnham, K. J. et al., J. Inorg. Chem. 1996, 35, 1065-1072; Lempers, E. L. M. and Reedijk, J., Adv. Inorg. Chem. 1991; 37:175-217; Andrews, P. A. et al., Anal. Biochem. 1984; 143:46-56; Dolman, R. C. et al., J. Inorg. Biochem, 2002; 88:260-267; Borch, R. F. and Pleasants, M. E. PNAS, 1979; 76:6611-6614).

Like other chemotherapeutics, systemic administration of cisplatin is associated with acute and long-term toxicities. Side effects include hearing loss, neuropathy, kidney damage, nausea, vomiting and hypomagnesemia (Baum, E. S. et al., Cancer Treat. Rep. 1981; 65:815-822; Brock, P. R. et al., Med. Pediatr. Oncol., 1991; 19:295-300; Hayes F. A. et al., Cancer Treat. Rep. 1979; 63:547-548).

Attempts to minimize deactivation and toxicity of cisplatin have included entrapment in liposomes. Steerenberg et al. have reported that cisplatin entrapped in liposomes exhibit increased stability and reduced toxicity relative to free (i.e., non-liposomal) cisplatin, while retaining efficacy (Steerenberg et al., International Journal of Pharmaceutics, 1087; 40:51-62; Steerenberg et al., Cancer Chemother. Pharmacol., 1988; 21:299-307). In addition, Chou et al. treated 19 patients suffering from relapsed osteosarcoma only in the lungs with an inhaled lipid cisplatin (ILC) and demonstrated that ILC was well tolerated (i.e., few side effects) and exhibited low systemic exposure compared to a dose of intravenous cisplatin (Chou et al., Pediatr Blood Cancer, 2012; DOI 10.1002/pbc). Although efficacy was not a primary objective, Chou et al. suggested that patient's with sustained benefit from ILC were limited to those with lesions ≤2 cm and those who underwent complete surgical resection of the tumor (Chou et al., Pediatr Blood Cancer, 2012; DOI 10.1002/pbc). Whether or not ILC has a role in the setting of minimal residual disease or as an adjuvant therapy is not known (Chou et al., Pediatr Blood Cancer, 2012; DOI 10.1002/pbc).

While surgical reconstruction techniques have improved considerably over the past decades, allowing limb salvage in most patients, chemotherapy still relies on the same drugs as in the early 1980's (Ritter and Bielack, Annals of Oncology, 2010; Supplement 7: vii320-325). Consequently, survival rates have not improved (Ritter and Bielack, Annals of Oncology, 2010; Supplement 7: vii320-325). Thus, additional treatments are needed to treat and cure patients suffering from pulmonary metastatic disease of recurrent osteosarcoma.

SUMMARY OF THE INVENTION

The present disclosure provides methods and compositions useful in treating pulmonary cancer.

According to one aspect, the described invention provides a method for treating pulmonary cancer in a subject in need thereof, comprising: (1) surgically excising the pulmonary cancer so that the subject is characterized as being macroscopically disease-free; and (2) administering by inhalation an inhalational lipid cisplatin (ILC) comprising a lipid-complexed cisplatin at a dose of from 18 mg/m$^2$ to 36 mg/m$^2$, wherein the ILC is dispersed throughout an aqueous phase of a dispersion.

According to another aspect, the described invention provides a method for treating pulmonary microscopic metastatic disease of osteosarcoma in a subject suffering from a primary osteosarcoma without a macroscopic lung metastasis, comprising: (1) surgically excising the primary osteosarcoma with or without treatment of combined systemic chemotherapies so that the subject is characterized as being macroscopically disease-free; and (2) administering by inhalation an inhalational lipid cisplatin (ILC) comprising a lipid-complexed cisplatin at a dose of from 18 mg/m$^2$ to 36 mg/m$^2$, wherein the ILC is dispersed throughout an aqueous phase of a dispersion.

According to one embodiment, the pulmonary cancer is pulmonary metastastic disease of osteosarcoma. According to another embodiment, the pulmonary metastatic disease of osteosarcoma is a recurrent osteosarcoma. According to another embodiment, the pulmonary cancer is non-small cell lung cancer (NSCLC). According to another embodiment, the NSCLC is bronchioloalveolar cancer.

According to one embodiment, the ILC further comprises liposomes. According to another embodiment, the liposomes comprise a sterol and a phosphatidylcholine. According to another embodiment, the sterol is cholesterol. According to another embodiment, the phosphatidylcholine is dipalmitoylphosphatidylcholine (DPPC).

According to one embodiment, the administering by inhalation is performed by a nebulizer. According to another embodiment, the administering by inhalation is at a dose of 36 mg/m$^2$. According to another embodiment, the administering by inhalation is at a dose of at least 24 mg/m$^2$. According to another embodiment, the administering by inhalation is at a dose of at least 18 mg/m$^2$. According to another embodiment, the administering by inhalation occurs at a rate of 0.3 mL/minute for 20 minutes. According to another embodiment, the administering by inhalation occurs 1 to 4 times per day every 14 days.

According to one embodiment, the dispersion has a particle size of ≤1 μm.

According to one embodiment, the subject has been previously treated with combined systemic chemotherapy and surgical excision of primary osteosarcoma. According to another embodiment, the subject has undergone surgical excision of a macroscopic lung metastasis. According to another embodiment, the macroscopic lung metastasis is a first pulmonary recurrence. According to another embodiment, the macroscopic lung metastasis is a pulmonary recurrence of the pulmonary cancer. According to another embodiment, the pulmonary recurrence is a second or subsequent pulmonary recurrence.

According to one embodiment, the method further comprises detecting the recurrent osteosarcoma by measuring a biomarker relative to a disease-free control. According to another embodiment, the biomarker is a biomarker found in systemic circulation. According to another embodiment, the systemic biomarker is selected from the group consisting of microRNA-21 (miRNA-21), microRNA-199a-3p (miRNA-199a-3p), microRNA-143 (miRNA-143), cluster of differentiation molecule 117 (CD117), Stro-1, bone-specific alkaline phosphatase (BALP), lactate dehydrogenase (LDH), and chondroitin sulfate epitope WF6 (WF6).

DETAILED DESCRIPTION OF THE INVENTION

The described invention can be better understood from the following description of exemplary embodiments, taken in conjunction with the accompanying figures and drawings. It should be apparent to those skilled in the art that the described embodiments of the described invention provided herein are merely exemplary and illustrative and not limiting.

Definitions

Various terms used throughout this specification shall have the definitions set out herein.

The term "administer", "administering" or "to administer" as used herein, refers to the giving or supplying of a medication, including in vivo administration, as well as administration directly to tissue or cells ex vivo. Generally, compositions may be administered systemically either orally, bucally, parenterally, topically, by inhalation or insufflation (i.e., through the mouth or through the nose) or rectally in dosage unit formulations containing conventional nontoxic pharmaceutically acceptable carriers, adjuvants and vehicles as desired, or may be locally administered by means such as, but not limited to, injection, implantation, grafting, topical application or parenterally.

The term "adverse event" or "AE" as used herein refers to any undesirable change from a patient's baseline condition associated with the use of a medical product in a patient. An undesirable change refers to any unfavorable or unintended sign including, but are not limited to, an abnormal laboratory finding, symptom or disease that occurs during the course of a study, whether or not considered related to the study drug, etc. The term "treatment-emergent AE" as used herein refers to any AE temporally associated with the use of a study drug, whether or not considered related to the study drug.

The term "aerosol" as used herein refers to a substance of fine solid or liquid particles suspended in gas and dispensed from a pressurized container.

The terms "agent" and "therapeutic agent" are used interchangeably herein to refer to a drug, molecule, composition, or other substance that provides a therapeutic effect. The term "active agent" as used herein, refers to the ingredient, component or constituent of the compositions of the described invention responsible for the intended therapeutic effect.

The term "albumin" as used herein refers to a protein made by the liver. A serum albumin test can determine if a patient has liver disease, kidney disease, or if the body is not absorbing enough protein. For example, the normal range of albumin in the blood is 3.4-5.4 g/dL. Lower than normal levels of serum albumin may be indicative of liver disease, kidney disease, Crohn's disease, Whipple's disease, etc.

The term "alkaline phosphatase" as used herein refers to is a hydrolase enzyme responsible for removing phosphate groups from many types of molecules including nucleotides, proteins, and alkaloids. An increase in alkaline phosphatase in the blood may be indicative of liver disease or bone disorders such as osteosarcoma, rickets, Paget's disease and the like.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptosis is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways.

The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligomerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation, can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway (Loberg, R D, et al., J. Biol. Chem. 277 (44): 41667-673 (2002)). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon aggregation and mitochondrial localization, induces cytochrome c release. Akt is a critical regulator of GSK-3, and phosphorylation and inactivation of GSK-3 may mediate some of the antiapoptotic effects of Akt.

The term "attached" as used herein refers to being fastened, fixed, joined, connected, bound, adhered to or assembled with.

The term "bicarbonate" as used herein refers to a chemical that regulates the pH of blood. Bicarbonate ($HCO_3$) prevents the pH of blood from becoming too acidic or too basic. Tests to measure bicarbonate levels in the blood may be performed to detect conditions that affect blood bicarbonate, including many kidney diseases, lung diseases and metabolic conditions.

The term "bilirubin" as used herein refers to a brownish yellow substance found in bile. Bilirubin is produced when the liver breaks down old red blood cells. Abnormal levels of bilirubin in blood may be indicative of, for example, liver disease, gallstones, pancreatic cancer or hemolytic anemia.

The term "biomarker" (or "biosignature") as used herein refers to a peptide, a protein, a nucleic acid, an antibody, a gene, a metabolite, or any other substance used as an indicator of a biologic state. It is a characteristic that is measured objectively and evaluated as a cellular or molecular indicator of normal biologic processes, pathogenic processes, or pharmacologic responses to a therapeutic intervention. The term "cancer biomarker" (or "cancer biosignature") as used herein refers to a peptide, a protein, a nucleic acid, an antibody, a gene, a metabolite, or any other substance used to detect the predisposition for, or the presence of, primary or metastatic cancer in a subject. For example, biomarkers useful in the detection of osteosarcoma include, but are not limited to, microRNA-21 (miRNA-21), microRNA-199a-3p (miRNA-199a-3p), microRNA-143 (miRNA-143), cluster of differentiation molecule 117 (CD117), Stro-1, bone-specific alkaline phosphatase (BALP), lactate dehydrogenase (LDH), chondroitin sulfate epitope WF6 (WF6) and the like.

The term "calcium" as used herein refers to a mineral that is essential to bones, teeth, heart, nerves, and blood clotting systems. Testing calcium levels in the blood may indicate problems with the parathyroid glands, kidneys or bone, pancreatitis, or cancers (e.g., osteosarcoma).

The term "capacity" as used herein refers to the amount of oxygen taken up by pulmonary capillary blood per minute per unit average oxygen gradient between alveolar gas and pulmonary capillary blood. The term "vital capacity" or "VC" as used herein refers to the greatest volume of air that can be exhaled from the lungs after a maximum inspiration. The term "forced vital capacity" or "FVC" as used herein refers to vital capacity measured with the subject exhaling as rapidly as possible.

The term "carbon monoxide diffusion capacity" or "$DL_{CO}$" as used herein refers to the lung's ability to take up an inhaled nonreactive test gas, such as carbon monoxide (CO), which binds to hemoglobin. $DL_{CO}$ is the rate of uptake of CO per driving pressure of alveolar CO and can be represented as: $DL_{CO}=V_{CO}/PA_{CO}$ where $V_{CO}$=the uptake of CO (mL/min); and $PA_{CO}$=the mean alveolar pressure of CO (mL of mercury). For example, obstructive airway disease, interstitial lung disease, and pulmonary vascular disease cause a decrease in $DL_{CO}$.

The term "carrier" or "pharmaceutically acceptable carrier" as used herein refer to a pharmaceutically acceptable inert agent or vehicle for delivering one or more active agents to a subject, and often is referred to as "excipient." The carrier must be of sufficiently high purity and of sufficiently low toxicity to render it suitable for administration to the subject being treated. The carrier further should maintain the stability and bioavailability of an active agent. The carrier can be liquid or solid and is selected, with the planned manner of administration in mind, to provide for the desired bulk, consistency, etc., when combined with an active agent and other components of a given composition.

The term "cell" is used herein to refer to the structural and functional unit of living organisms and is the smallest unit of an organism classified as living.

The term "cholesterol" as used herein refers to a waxy, fat-like substance found in all cells of the body. Cholesterol is the principal sterol synthesized by animals and is an essential structural component of animal cell membranes as well as a precursor for the biosynthesis of steroid hormones, bile acids and vitamin D.

The term "cisplatin" or "cis-diaminedichloroplatinum (II)" as used herein refers to the platinum-based anticancer chemotherapy drug that acts as an alkylating agent.

The term "compatible" as used herein means that the components of a composition are capable of being combined with each other in a manner such that there is no interaction that would substantially reduce the efficacy of the composition under ordinary use conditions.

The term "complete blood count" or "CBC" as used herein refers to a laboratory test that provides detailed information about the amount and the quality of each of the blood cell types. It usually includes a measurement of each of the three major blood cells (red blood cells, white blood cells, and platelets) and a measure of the hemoglobin and hematocrit. "Hemoglobin" (HGB) refers to the number of grams of hemoglobin in a deciliter of blood (g/dL). Normal hemoglobin levels in healthy adult human subjects are about 14 g/dL to about 18 g/dL for men and about 12 g/dL to about 16 g/dL for women. As a rough guideline, hemoglobin generally should be about one-third the hematocrit. "Red Blood Cell Count" (RBC) refers to the total number of red blood cells in a quantity of blood. Normal ranges in human subjects are about 4.5 million cells/mm$^3$ to about 6.0 million cells/mm$^3$ for men and about 4.0 million cells/mm$^3$ to about 5.5 million cells/mm$^3$ for women. "White Blood Cell Count" (WBC) refers to the total number of white blood cells or leukocytes in a quantity of blood. Normal ranges in human subjects are about $4.3 \times 10^3$ cells/mm3 to about $10.8 \times 10^3$ cells/mm$^3$. "Hematocrit" (HCT) refers to the proportion of red blood cells as a percentage of total blood volume. A normal hematocrit for human subjects is about 40% to about 55% for men and about 35% to about 45% for women.

The term "component" as used herein refers to a constituent part, element or ingredient.

The terms "composition" and "formulation" are used interchangeably herein to refer to a product of the described invention that comprises all active and inert ingredients. The term "active" refers to the ingredient, component or constituent of the compositions of the described invention responsible for the intended therapeutic effect. The terms "pharmaceutical formulation" or "pharmaceutical composition" as used herein refer to a formulation or composition that is employed to prevent, reduce in intensity, cure or otherwise treat a target condition or disease.

The term "condition" as used herein, refers to a variety of health states and is meant to include disorders or diseases caused by injury or any underlying mechanism or disorder.

The term "contact" and its various grammatical forms as used herein refers to a state or condition of touching or of immediate or local proximity. Contacting a composition to a target destination may occur by any means of administration known to the skilled artisan.

The term "creatinine" as used herein refers to the waste product from the normal breakdown of muscle tissue. Tests to check blood levels of creatinine are used to determine renal function.

The term "delay", "delaying", "delayed" or "to delay" as used herein, refers to stopping, detaining or hindering for a time; to cause to be slower or to occur more slowly than normal.

The term "derivative" as used herein, refers to a compound that may be produced from another compound of similar structure in one or more steps. A "derivative" or "derivatives" of a compound retain(s) at least a degree of the desired function of the compound. Accordingly, an alternate term for "derivative" may be "functional derivative." Derivatives can include chemical modifications, such as alkylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "dipalmitoylphosphatidylcholine" or "DPPC" as used herein refers to a phospholipid consisting of two palmitic acids and is the major constituent of pulmonary surfactants.

The term "disease" or "disorder" as used herein refers to an impairment of health or a condition of abnormal functioning.

The term "dispersion" as used herein refers to a two-phase system, in which one phase is distributed as liquid droplets in the second, or continuous phase. In these systems, the dispersed phase frequently is referred to as the discontinuous or internal phase, and the continuous phase is called the external phase and comprises a continuous process medium. For example, in course dispersions, the particle size is 0.5 μm. In colloidal dispersions, the size of the dispersed particle is in the range of approximately 1 nm to 0.5 μm. A molecular dispersion is a dispersion in which the dispersed phase consists of individual molecules; if the molecules are less than colloidal size, the result is a true solution.

The term "event-free survival" or "EFS" as used herein refers to the time from diagnosis of the prior pulmonary relapse to diagnosis of any subsequent relapse or death.

The term "forced expiratory volume" or "FEV" as used herein refers to the maximum amount of air that can be expelled in a given number of seconds during a forced vital capacity (VC) determination. It is usually given as FEV followed by a subscript indicating the number of seconds over which the measurement is made, although it is sometime given as a percentage of forced vital capacity (FVC).

The terms "functional equivalent" or "functionally equivalent" are used interchangeably herein to refer to substances, molecules, polynucleotides, proteins, peptides, or polypeptides having similar or identical effects or use.

The term "improve" (or improving) as used herein refers to bring into a more desirable or excellent condition.

The term "inhalation", "inhale" or "inhaled" as used herein refers to the act of drawing a material (e.g. medication) into the lungs.

The term "injury" as used herein, refers to damage or harm to a structure or function of the body caused by an outside agent or force, which may be physical or chemical.

The term "isolate" and its various grammatical forms as used herein refers to placing, setting apart, or obtaining a protein, molecule, substance, nucleic acid, peptide, cell or particle, in a form essentially free from contaminants or other materials with which it is commonly associated, separate from its natural environment.

The term "Kaplan Meier plot" or "Kaplan Meier survival curve" as used herein refers to the plot of probability of clinical study patients surviving in a given length of time while considering time in many small intervals. The Kaplan Meier plot assumes that: (i) at any time patients who are censored (i.e., lost) have the same survival prospects as patients who continue to be followed; (ii) the survival probabilities are the same for patients recruited early and late in the study; and (iii) the event (e.g., death) happens at the time specified. Probabilities of occurrence of event are computed at a certain point of time with successive probabilities multiplied by any earlier computed probabilities to get a final estimate. The survival probability at any particular time is calculated as the number of patients surviving divided by the number of patients at risk. Patients who have died, dropped out, or have been censored from the study are not counted as at risk.

The term "lactate dehydrogenase" as used herein refers to an enzyme that helps produce energy in almost all tissues of the body. Lactate dehydrogenase (LDH) levels measured in the blood may help diagnose lung disease, lymphoma, anemia, liver disease and may help determine the efficacy of chemotherapy especially during treatment for lymphoma.

The term "lipid" as used herein refers to a fatty or waxy organic compound that is readily soluble in nonpolar solvents. Examples of lipids include, but are not limited to, waxes, oils, sterols, cholesterol, fat-soluble vitamins, monoglycerides, diglycerides, triglycerides (fats) phospholipids, fatty acids, isoprenoid compounds, hormones, carotenes and eicosanoids. The term "anionic lipid" as used herein refers to a lipid that has a net negative charge. Examples of anionic lipids include, but are not limited to, phosphatidylglycerol, phosphatidylinositol, cardiolipin, phosphatidylserine, and the like. The term "cationic lipid" as used herein refers to a lipid that has a net positive charge. Exemplary cationic lipids include, without limitation, N-[1-(2,3-dioleyloxy)propyl]-N,N,N-trimethylammonium chloride (DOTMA), [1,2-bis(oleoyloxy)-3-(trimethylammonio)propane] (DOTAP), 3β[N—(N',N'-dimethylaminoethane)carbamoyl]-cholesterol (DC-Chol), and dioctadecylamidoglycylspermine (DOGS). The term "neutral lipid" as used herein refers to a lipid that has no net charge. Examples of neutral lipids include, but are not limited to, phosphatidylethanolamine, sphingomyelin, glycolipids, cerebrosides, gangliosides, dipalmitoylphosphatidylcholine (DPPC), cholesterol, and the like.

The term "lipid-complex" or "lipid-complexed" as used herein refers to an agent associated with, bound to, or coordinated with a lipid moiety.

The term "liposome", "liposome delivery system" or "liposome drug delivery system" as used herein refers to a vesicle composed of one or more concentric phospholipid bilayers used to deliver microscopic substances (e.g., drugs) to cells.

The term "metastasis" or "metastases" as used herein refers to tumor growth or deposit that has spread via lymph or blood to an area of the body remote from the primary tumor. The term "macroscopic lung metastases" as used herein refers to metastases of osteosarcoma deposited in the lung that are large enough to be perceived by the unaided eye.

The term "metastatic osteosarcoma" as used herein refers to osteosarcoma that has spread from its site of origin to one or more sites elsewhere in the body, usually by way of the blood vessels or the lymphatic system. The term "metastasectomy" as used herein refers to surgery to remove one or more metastasis.

The term "modulate" as used herein means to regulate, alter, adapt, or adjust to a certain measure or proportion.

The term "nebulize" or "nebulization" as used herein refers to the conversion of a liquid into an aerosol or spray, used for example, for medical treatment.

The term "nebulizer" as used herein refers to a device for producing a fine spray of liquid, used for example, for inhaling a medicinal drug.

The term "nucleic acid" as used herein refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" as used herein refers to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The term "overall survival" or "OS" as used herein refers to the time from diagnosis of a prior pulmonary relapse to death from any cause.

The term "particle", as used herein, refers to extremely small constituents, (e.g., nanoparticles or microparticles) that may contain in whole or in part therapeutic agent(s). The particles may contain therapeutic agent(s) in a core surrounded by a coating. Therapeutic agent(s) also may be dispersed throughout the particles. Therapeutic agent(s) also may be adsorbed into the particles. The particles may be of any order release kinetics, including zero order release, first order release, second order release, delayed release, sustained release, immediate release, etc., and any combination thereof. The particle may include, in addition to therapeutic agent(s), any of those materials routinely used in the art of pharmacy and medicine, including, but not limited to, erodible, nonerodible, biodegradable, or nonbiodegradable material or combinations thereof. The particles may be microcapsules that contain the therapeutic agent(s) in a solution or in a semi-solid state. The particles may be of virtually any shape.

The term "phosphatidylcholine" as used herein refers to a phospholipid that is a major component of cellular membranes and functions in the transport of lipoproteins in tissues. Examples of phosphatidylcholine include, but are not limited to dipalmitoylphosphatidylcholine (DPPC).

The term "portion" as used herein refers to a part of a whole separated from or integrated with it.

The term "prevent", "preventing", "prevented" or "to prevent" as used herein, refers to effectual stoppage of action or progress.

The term "primary osteosarcoma" or "localized osteosarcoma" as used herein refers to osteosarcoma located at its site of origin (i.e., bone).

The term "prolong", "prolonging", "prolonged" or "to prolong" as used herein, refers to lengthening in time, extent, scope or range.

The term "propagate" as used herein refers to reproduce, multiply, or to increase in number, amount or extent by any process.

The term "purification" as used herein refers to the process of isolating or freeing from foreign, extraneous, or objectionable elements.

The term "recurrence" or "relapse" are used interchangeably herein to refer to the return of a cancer after treatment and after a period of time during which the cancer cannot be detected. The term "pulmonary recurrence", "pulmonary relapse", "pulmonary recurrent osteosarcoma", "pulmonary metastatic disease of recurrent osteosarcoma" or "pulmonary relapse osteosarcoma" as used herein refers to the return of osteosarcoma to lung tissue after treatment and after a period of time during which the osteosarcoma cannot be detected.

The term "reduce", "reducing", "reduced" or "to reduce" as used herein, refers to a diminishing, a decrease in, an attenuation or abatement of the degree, intensity, extent, size, amount, density or number of The term "relapse free interval" or "RFI" as used herein refers to the period from diagnosis of the prior pulmonary relapse to diagnosis of any subsequent relapse. In the case of pulmonary RFI (pRFI) and extrapulmonary RFI (eRFI), the subsequent relapse must be pulmonary or extrapulmonary respectively.

The term "relative" as used herein refers to something having, or standing in, some significant association to something else. The term "relative frequency" as used herein refers to the rate of occurrence of something having or standing in some significant association to the rate of occurrence of something else. For example, two cell types, X cells and Y cells occupy a given location. There are 5 X cells and 5 Y cells in that location. The relative frequency of cell type X is 5/10; the relative frequency of cell type Y is 5/10 in that location. Following processing, there are 5 X cells, but only 1 Y cell in that location. The relative frequency of cell type X following processing is 5/6, and the relative frequency of cell type Y following processing is 1/6 in that location.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function. In some embodiments "repair" includes full repair and partial repair.

The term "risk factor" as used herein refers to anything that raises the chances of a person developing a disease.

The term "serum glutamic oxaloacetic transaminase" as used herein refers to an enzyme that is normally present in liver and heart cells. Serum glutamic oxaloacetic transaminase (SGOT) is released into the blood when the liver or heart is damaged. Thus, elevated levels of SGOT in the blood are indicative of disease of or damage to the liver or heart.

The term "serum glutamic pyruvic transaminase" as used herein refers to an enzyme that is normally present in liver and heart cells. Serum glutamic pyruvic transaminase (SGPT) is released into the blood when the liver or heart is damaged. Thus, elevated levels of SGPT in the blood are indicative of disease of or damage to the liver or heart.

The term "side effects" as used herein refers to the unintended action(s) of a drug.

The term "Simon Two-Stage Optimal Design" as used herein refers to the designs proposed by Richard Simon for use in phase II clinical trials. Simon proposed two criteria, minimax and optimal, for selecting sample sizes and critical values. The maximum sample size and the expected sample size under a null hypothesis ($H_0$) are minimized in the minimax and optimal designs respectively. The expected sample size is minimized if the regimen has low activity subject to constraints upon the size of the type 1 and type 2 errors (Simon, R., Controlled Clinical Trials, 1989; 10:1-10).

The term "sterol" as used herein refers to any of a group of predominantly unsaturated solid alcohols of the steroid group, such as cholesterol, ergosterol and the like, present in the fatty tissue of plants and animals.

The term "stimulate" as used herein refers to activate, provoke, or spur. The term "stimulating agent" as used herein refers to a substance that exerts some force or effect.

The terms "subject" and "patient" are used interchangeably herein to refer to animal species of mammalian origin that may benefit from the administration of a drug composition or method of the described invention. Examples of subjects include humans, and other animals such as horses, pigs, cattle, dogs, cats, rabbits, mice, rats and aquatic mammals.

The phrase "subject in need thereof" as used herein refers to a subject suffering from a disease, disorder, condition or injury characterized by damaged or cancerous differentiated cells that (i) will be administered a pharmaceutical composition of the described invention, (ii) is receiving a pharmaceutical composition of the described invention; or (iii) has received a pharmaceutical composition of the described invention, in order to treat the condition, unless the context and usage of the phrase indicates otherwise.

The term "syndrome" as used herein, refers to a pattern of symptoms indicative of some disease or condition.

The term "technetium-99 m", "Tc-99 m" or "99 mTc" as used herein refers to a radioisotope of technetium which decays by isomeric transition, emitting an essentially monoenergetic gamma ray of 142 kev with a half-life of 6.01 h. The term "technetium bone scan" as used herein refers to the use of technetium-99m (Tc-99m or $^{99m}$Tc) as an imaging tracer to scan bone for injury or disease (e.g., cancer).

The terms "therapeutic amount", "therapeutically effective amount" and "amount effective" are used interchangeably herein to refer to an amount of one or more active agent(s) that is sufficient to provide the intended benefit of treatment. Dosage levels are based on a variety of factors, including the type of injury, the age, sex, weight, medical condition of the patient, the severity of the condition, the route of administration and the particular active agent employed. The dosage regimen may vary widely, but can be determined routinely by a physician using standard methods.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The term "treat", "treating" or "to treat" as used herein, refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and (e) limiting recurrence of symptoms in patients that were previously asymptomatic for the disorder. The term "treat", "treating" or "to treat" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms.

The present disclosure provides methods and compositions useful in the treatment of pulmonary metastatic disease of recurrent osteosarcoma.

According to some embodiments, the described invention provides a method for treating recurrent osteosarcoma of the lung in a subject in need thereof, comprising administering to the subject by inhalation a therapeutic amount of a sterile pharmaceutical composition comprising a chemotherapeutic agent. According to some embodiments, the chemotherapeutic agent is cisplatin. According to some embodiments, the cisplatin can be complexed to a lipid moiety. According to some embodiments, the lipid-complexed cisplatin is associated with a liposome. According to some embodiments, the lipid-complexed cisplatin is encapsulated by a liposome. Cisplatin is available from commercial suppliers of pharmaceutical materials (e.g., Johnson Matthey, West Deptford, N.J.).

The compositions of the described invention may be used in the form of drops or sprays (e.g., a nasal spray, aerosol spray, or pump spray) or other vehicles for inhalation or nasal administration (intranasal delivery). Aerosol spray preparations can be contained in a pressurized container with a suitable propellant such as a hydrocarbon propellant. Pump spray dispensers can dispense a metered dose or a dose having a specific particle or droplet size. Any dispensing device can be arranged to dispense only a single dose, or a multiplicity of doses. More generally, compositions of the invention formulated for inhalation or intranasal administration, can also be provided as solutions, suspensions, or viscous compositions.

The compositions of the described invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotohaler brand powder inhaler or Fison's Spinhaler® brand powder inhaler. Another suitable unit-dose container that provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

According to some embodiments, the compositions of the described invention can be delivered by other instruments. Examples include, but are not limited to, a nebulizer (e.g., LC Star Reusable Nebulizer, part number 022F51, Pari USA, Midlothian, Va.), an insufflator, an inhaler or puffer.

According to some embodiments, the compositions of the described invention may be formulated with an excipient or carrier selected from solvents, suspending agents, binding agents, fillers, lubricants, disintegrants, and wetting agents/surfactants/solubilizing agents. The terms "excipient" or "carrier" refer to substances that do not deleteriously react with the glucagon-depleting compounds. Carriers must be of sufficiently high purity and of sufficiently low toxicity to render them suitable for administration to the subject being treated. The carrier can be inert, or it can possess pharmaceutical benefits.

The carrier can be liquid or solid and is selected with the planned manner of administration in mind to provide for the desired bulk, consistency, etc., when combined with an active and the other components of a given composition. Typical pharmaceutical carriers include, but are not limited to, binding agents (including, but not limited to pregelatinized maize starch, polyvinylpyrrolidone or hydroxypropyl methylcellulose); fillers (including but not limited to lactose and other sugars, microcrystalline cellulose, pectin, gelatin, calcium sulfate, ethyl cellulose, polyacrylates or calcium hydrogen phosphate.); lubricants (including, but not limited to magnesium stearate, talc, silica, sollidal silicon dioxide, stearic acid, metallic stearates, hydrogenated vegetable oils, corn starch, polyethylene glycols, sodium benzoate, sodium acetate); disintegrants (including, but not limited to, starch, sodium starch glycolate) and wetting agents (including but not limited to sodium lauryl sulfate). Additional suitable carriers for the compositions of the described invention include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like, which do not deleteriously react with the active agents.

The term "pharmaceutically acceptable carrier" as used herein refers to any substantially non-toxic carrier conventionally useful for administration of pharmaceuticals in which the active agent will remain stable and bioavailable. According to some embodiments, the pharmaceutically acceptable carrier of the compositions of the described invention include a release agent such as a sustained release or delayed release carrier. According to some embodiments, the carrier can be any material capable of sustained or delayed release of the active agent of the described invention to provide a more efficient administration, resulting in less frequent and/or decreased dosage of the active ingredient, ease of handling, and extended or delayed effects. Non-limiting examples of such carriers include lipids, liposomes, microsponges, microspheres, or microcapsules of natural and synthetic polymers and the like. According to some embodiments, the compositions of the described invention further comprise a liposome. It is understood that the liposome comprises at least one lipid. The lipid can be the same as or different from the lipid in the lipid-complexed cisplatin. According to some embodiments, liposomes may be formed from a variety of phospholipids such as cholesterol, stearylamines or phosphatidylcholines.

The lipids used in the described invention can be synthetic, semi-synthetic or naturally-occurring lipids, including phospholipids, tocopherols, sterols, fatty acids, glycolipids, negatively-charged lipids, cationic lipids or neutral lipids. Exemplary phospholipids include, without limitation, egg phosphatidylcholine (EPC), egg phosphatidylglycerol (EPG), egg phosphatidylinositol (EPI), egg phosphatidylserine (EPS),phosphatidylethanolamine (EPE), and phosphatidic acid (EPA); soya counterparts, soy phosphatidyl choline (SPC); SPG, SPS, SPI, SPE, and SPA; hydrogenated egg and soya counterparts (e.g., HEPC, HSPC), stearically modified phosphatidylethanolamines, cholesterol derivatives, carotinoids, other phospholipids made up of ester linkages of fatty acids in glycerol positions 2 and 3 containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation. According to some embodiments, compositions of the described invention can include dipalmitoylphosphatidcholine (DPPC), a major constituent of naturally-occurring lung surfactant. Other examples include dimyristoylphosphatidycholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleylphosphatidyl-ethanolamine (DOPE) and mixed phospholipids such as, for example, palmitoylstearoylphosphatidylcholine (PSPC), palmitoylstearolphosphatidylglycerol (PSPG), triacylglycerol, diacylglycerol, seranide, sphinosine, sphingomyelin and single acylated phospholipids, for example, mono-oleoyl-phosphatidylethanolamine (MOPE).

Compositions of the described invention also can be readily prepared using technology known in the art, such as described in Remington's Pharmaceutical Sciences, 18th or 19th editions, published by the Mack Publishing Company of Easton, Pa., which is incorporated herein by reference.

According to some embodiments, the compositions of the described invention can further include one or more compatible active ingredients in addition to cisplatin, which are aimed at providing the composition with another pharmaceutical effect in addition to that provided by cisplatin. "Compatible" as used herein means that the active ingredients of such a composition are capable of being combined with each other in such a manner so that there is no interaction that would substantially reduce the efficacy of each active ingredient or the composition under ordinary use conditions. Examples of other therapeutic agents include, but are not limited to, chemotherapeutics, radiopharmaceuticals, immunomodulators and stem cells. Examples of chemotherapeutics include, but are not limited to, methotrexate, doxorubicin, carboplatin, etoposide, ifosfamide, cyclophosphamide, epirubicin, gemcitabine, and topotecan. Examples of radiopharmaceuticals include, but are not limited to, samarium-153 and strontium-89. Examples of immunomodulators include, but are not limited to, α-interferon and muramyl tripeptide phosphatidyl ethanolamine (MTP). Examples of stem cells include, but are not limited to, embryonic stem cells, somatic or adult stem cells, and induced pluripotent stem cells (IPSC). Sources of stem cells include, for example, autologous, allogeneic, and syngeneic.

A composition of the described invention, alone or in combination with other active ingredients, may be administered to a subject in a single dose or multiple doses over a period of time. As used herein, the terms "therapeutic amount," "therapeutically effective amount," and "pharmaceutically effective amount" are used interchangeably to refer to the amount of the composition of the invention that results in a therapeutic or beneficial effect, following its administration to a subject.

The concentration of the active substance is selected so as to exert its therapeutic effect, but low enough to avoid unacceptable side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the described invention to be used for an intended purpose.

A skilled artisan can determine a pharmaceutically effective amount of the inventive compositions by determining the unit dose. As used herein, a "unit dose" refers to the amount of the described composition required to produce a response of 50% of maximal effect (i.e. ED50). The unit dose can be assessed by extrapolating from dose-response curves derived from in vitro or animal model test systems. The amount of compounds in the compositions of the described invention that will be effective in the treatment of a particular disorder or condition will depend on the nature of the disorder or condition, and can be determined by standard clinical techniques (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the described invention are those large enough to produce the desired therapeutic effect. The therapeutically effective amount of the compositions of the described invention is administered one or more times per day on a regular basis.

According to some embodiments, the composition of the described invention can be used in combination with other treatment techniques. Such techniques include, but are not limited to, surgery and radiation therapy. Radiation therapy includes, for example, external beam radiation therapy, intensity modulated radiation therapy (IMRT, conformal proton beam therapy, and the like.

According to one embodiment, a subject in need thereof has a history of osteosarcoma metastatic to the lung(s). According to another embodiment, a subject in need thereof has a first or second pulmonary recurrence(s) removed by surgery. According to another embodiment, a subject in need thereof has been previously treated with a second-line chemotherapy. According to another embodiment, a subject in need thereof will be macroscopically disease free following pulmonary metastasectomy of a single lesion. According to another embodiment, a subject in need thereof will be macroscopically disease free following pulmonary metastasectomy of multiple lesions.

According to one embodiment, a study subject will be a patient who has had a first or second pulmonary recurrence and is currently macroscopically disease free following pulmonary metastasectomy. According to another embodiment, a study subject will be a patient who has not experienced a first pulmonary recurrence following surgical recision of the primary extrapulmonary tumor. According to another embodiment, a study subject will be a patient suffering from non-small cell lung cancer (NSCLC).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise. All technical and scientific terms used herein have the same meaning The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Selection of Eligible Subjects

The study populations will be (1) osteosarcoma patients who have been previously treated with systemic chemotherapy and surgical excision of the primary bone lesion(s); and (2) patients with recurrent osteosarcoma who have been previously treated with combined systemic chemotherapy and surgical excision of the primary bone lesion(s) and who have recently undergone successful surgical excision of all macroscopic lung metastases of their first or subsequent pulmonary recurrence.

Inclusion Criteria

1) History of Osteosarcoma metastatic to the lung(s). (First or second pulmonary recurrence(s) removed by surgery, and previous second-line systemic chemotherapy will be allowed).
2) Patients will be macroscopically disease free following pulmonary metastasectomy of a single or multiple lesions. Complete Remission surgically (free of macroscopic disease) will be required. Pleural disruption and/or microscopic positive margins will be allowed.
3) Age ≥13 years.
4) Patients will have recovered sufficiently from all acute adverse effects of prior therapies, excluding alopecia.
5) Patients will have an Eastern Cooperative Oncology Group (ECOG) performance status of 0-2 (Lansky score of 50-100 if <16 years old).
6) Patients will have recovered sufficiently from surgery and will have adequate airflow and pulmonary reserve. This decision should be at the investigator's discretion taking into consideration pre-surgery pulmonary function. (As a guideline: adequate airflow defined by a measured Forced Expiratory Volume (FEV1) not less than 50% of the predicted value and adequate pulmonary reserve as evidenced by a FEV1/FVC ratio of 65% or greater).
7) Patients will have adequate renal function as defined by a serum creatinine of ≤1.5 mg/dl.
8) Patients will have adequate liver function as defined by total bilirubin of ≤1.5 mg/dl and alanine aminotransferase (ALT) or aspartate aminotransferase (AST)<2.5 times the institution's upper normal limit.

9) Patients will have adequate bone marrow function as defined by an absolute neutrophil count (ANC) of ≥1,000/mm$^3$ and platelet count of ≥100,000/mm$^3$.

10) Signed informed consent including, where applicable, the consent of the patient's legal guardian.

TABLE 1

ECOG Performance Status Scale
ECOG PERFORMANCE STATUS*

| Grade | ECOG |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all self-care but unable to carry out any work activities. Up and about more than 50% of waking hours |
| 3 | Capable of only limited self-care, confined to bed or chair more than 50% of waking hours |
| 4 | Completely disabled. Cannot carry on any self-care. Totally confined to bed or chair |
| 5 | Dead |

*Oken, M. M. et al., Toxicity and Response Criteria of the Eastern Cooperative Oncology Group. Am. J. Clin. Oncol. 5: 649-655 (1982)

TABLE 2

Lansky Performance Status Scale
LANSKY PERFORMANCE STATUS FOR CHILDREN*

| | |
|---|---|
| 100 | Fully active, normal |
| 90 | Minor restrictions in strenuous physical activity |
| 80 | Active, but tired more quickly |
| 70 | Greater restriction of play and less time spent in play activity |
| 60 | Up and around, but active play minimal; keeps busy by being involved in quieter activities |
| 50 | Lying around much of the day, but gets dressed; no active playing; participates in all quiet play and activities |
| 40 | Mainly in bed; participates in quiet activities |
| 30 | Bedbound; needing assistance even for quiet play |
| 20 | Sleeping often; play entirely limited to very passive activities |
| 10 | Doesn't play; does not get out of bed |
| 0 | Unresponsive |

*Lansky, S. B. et al., The Measurement of Performance in Childhood Cancer Patients. Cancer 60 (7): 1651-1656 (1987)

Exclusion Criteria

1) Current extrapulmonary disease.

2) Current macroscopic pulmonary lesions.

3) Greater than 2 pulmonary recurrences.

4) Greater than 4 weeks since thoracotomy rendering patient free of macroscopic disease.

5) Females who are pregnant or breast-feeding.

6) Concomitant disease or condition that could interfere with the conduct of the study, or that would, in the opinion of the investigator, pose an unacceptable risk to the patient in this study.

7) Contraindication to or unwillingness to undergo multiple computerized tomography (CT) scans and chest X-rays.

8) Unwillingness or inability to comply with the study protocol for any other reason.

9) Participation in an investigational drug or device study, or other anti-neoplastic therapy within 14 days of the first day of dosing on this study.

Example 2

Treatment Regimen

Inhalational lipid cisplatin (ILC) is prepared by repetitive cycles of cooling and heating as described in PCT/US2005/040489, published as WO2006/055352, which is incorporated herein by reference. The process for producing lipid-based platinum compound formulations can comprise mixing a platinum compound with an appropriate hydrophobic matrix and subjecting the mixture to one or more cycles of two separate temperatures. The process is believed to form active platinum compound associations. For example, in aqueous solution, when the platinum compound is cisplatin, it may form large insoluble aggregates with a diameter of greater than a few microns. In the presence of an amphipathic matrix system, such as a lipid bilayer, cisplatin-lipid associations form. For example, the associations may be formed in the internal aqueous space, the hydrocarbon core region of a lipid bilayer, or the liposome interface or headgroup. During the warming cycle of the process, it is believed that cisplatin is returned to solution at a greater rate in aqueous regions of the process mixture than from the lipid-matrix. As a result of applying more than one cool/warm cycle, cisplatin further accumulates in the lipid-matrix. Without being limited by theory, experimentation indicates that the cisplatin-lipid associations cause the immediate surroundings of the interfacial bilayer region to be more hydrophobic and compact. This results in a high level of entrapment of active platinum compound as cooling and warming cycles are repeated.

Without being bound by a particular theory, it is believed that during repetitive cooling/heating, cisplatin is solubilized and crystallized repetitively. For example, as soluble cisplatin is cooled, some portion enters complexes with the lipid while the remainder precipitates. Upon subsequent heating, unencapsulated cisplatin that is crystallized becomes soluble again and enters complexes with the lipid. Encapsulated cisplatin substantially stays in the lipid complex during the cooling/heating cycle (i.e., no appreciable amount leaves the lipid complex during the heating phase).

Dose Calculation

The dose of ILC will be based on body surface area (BSA) as calculated from actual body weight and height prior to each course. The BSA should be capped at a maximum of 2.0 m$^2$ for larger patients. The starting dose for all patients will be 36 mg/m$^2$.

Administration of ILC

ILC will be administered on an outpatient basis unless hospitalization is required for another reason. The ILC dose will be administered by inhalation via nebulizer over 1 day which starts a 14-day cycle. The dose frequency of ILC administration is every 14 days.

ILC will be administered by inhalation. A dose of 36 mg/m$^2$ will require up to 4 nebulizations for a treatment cycle. The nebulizations may be grouped, with a rest after each group of nebulizations. A single nebulization takes approximately 20-minutes. Treatment will be repeated every 14 days. Patients will be monitored for toxicity. Anti-emetics may be prescribed to patients as per institutional guidelines prior to administration of ILC.

Duration of Therapy

Treatment will continue until:

1) new pulmonary lesions are detected (patients developing new pulmonary lesions may remain on study until the lesion has been resected and histologically confirmed to be osteosarcoma, at which time the patient should be removed from the study (the date of recurrence will be the date of the imaging procedure which first identified the new lesion). If there is histological evidence of necrosis of the lesion, which is considered to be due to ILC therapy, the patient may remain on study at the Investigator's discretion. If the new lesion is not osteosarcoma, the lesion will not be considered as recurrence and the patient may continue on study as long as alternative chemotherapy is not indicated for the new lesion;

2) extrapulmonary recurrence (at the investigator's discretion, patients experiencing extrapulmonary recurrence may remain on therapy, if it is considered that ILC treatment is providing clinical benefit in the lungs, and no other systemic chemotherapy is to be prescribed);

3) unacceptable toxicity occurs;

4) patient or physician decide to terminate.

Example 3

Non-Small Cell Lung Cancer (NSCLC) Patients

ILC can be used as a first-line, as a neoadjuvant (i.e., before surgery) or as an adjuvant (i.e., after surgical resection of primary lung tumor) treatment for patients suffering from non-small cell lung cancer (NSCLC). NSCLC patients may, in addition, also receive adjuvant systemic chemotherapy (e.g., IV cisplatin), to treat existing disease and prevent recurrence.

Like with osteosarcoma, NSCLC patients will be treated after the resection of all macroscopic disease, to prevent or delay pulmonary recurrence.

A particular histologic subtype (about 5%) of NSCLC is "bronchioloalveolar carcinoma" (BAC). BAC does not usually spread outside the lungs. BAC patients with resectable tumors will be treated with ILC as a neoadjuvant and/or adjuvant treatment to improve the results of surgery (i.e., to prevent future local lung recurrence). BAC patients with non-resectable tumors will be treated with ILC either alone or in combination with systemic cisplatin, to slow or halt local lung progression.

While the described invention has been described with reference to the specific embodiments thereof, it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for treating a subject suffering from osteosarcoma with lung metastasis, where the subject has not previously been treated with an inhalational lipid cisplatin (ILC), the method consisting of:
    (1) first surgically excising the osteosarcoma from the lungs of the subject so that the subject is macroscopically disease-free; and
    (2) then administering by inhalation via a nebulizer the ILC comprising a lipid-complexed cisplatin at a dose of from 18 mg/m$^2$ to 36 mg/m$^2$ given 1 to 4 times during the same day, with the dose frequency every 14 days, wherein the ILC is dispersed throughout an aqueous phase of a dispersion.

2. The method according to claim 1, wherein a lipid-complexed cisplatin is encapsulated by a liposome.

3. The method according to claim 2, wherein the liposome comprises a sterol and a phosphatidylcholine.

4. The method according to claim 3, wherein the sterol is cholesterol.

5. The method according to claim 3, wherein the phosphatidylcholine is dipalmitoylphosphatidylcholine (DPPC).

6. The method according to claim 1, wherein the administering by inhalation is at a dose of 36 mg/m$^2$.

7. The method according to claim 1, wherein the administering by inhalation is at a dose of at least 24 mg/m$^2$.

8. The method according to claim 1, wherein the administering by inhalation is at a dose of at least 18 mg/m$^2$.

9. The method according to claim 1, wherein the dispersion has a particle size of <1 μm.

10. The method according to claim 1, wherein the administering by inhalation occurs at a rate of 0.3 mL/minute for 20 minutes.

11. The method according to claim 1, wherein the osteosarcoma is detected by measuring a biomarker relative to a disease-free control.

12. The method according to claim 11, wherein the biomarker is a biomarker found in systemic circulation.

13. The method according to claim 12, wherein the biomarker is selected from the group consisting of microRNA-21 (miRNA-21), microRNA-199a-3p (miRNA-199a-3p), microRNA-143 (miRNA-143), cluster of differentiation molecule 117 (CD117), Stro-1, bone-specific alkaline phosphatase (BALP), lactate dehydrogenase (LDH), and chondroitin sulfate epitope WF6 (WF6).

14. The method according to claim 1, wherein said subject is suffering from Recurrent/Relapse Osteosarcoma.

* * * * *